(12) United States Patent
Findlay et al.

(10) Patent No.: US 10,870,817 B2
(45) Date of Patent: Dec. 22, 2020

(54) PERACID-CONTAINING PARTICLE

(71) Applicant: SOCIETA CHIMICA BUSSI S.P.A., Bussi sul Tirino (IT)

(72) Inventors: Paul Hugh Findlay, Deeside (GB); David Alan Pears, Deeside (GB); David John Duncalf, Deeside (GB); Melanie Jane Hughes, Deeside (GB); Lisa Elizabeth Scullion, Deeside (GB)

(73) Assignee: SOCIETA CHIMICA BUSSI S.P.A., Bussi sul Tirino (IT)

( * ) Notice: Subject to any disclaimer, the term of this patent is extended or adjusted under 35 U.S.C. 154(b) by 281 days.

(21) Appl. No.: 15/116,361

(22) PCT Filed: Feb. 10, 2015

(86) PCT No.: PCT/GB2015/050364
§ 371 (c)(1),
(2) Date: Aug. 3, 2016

(87) PCT Pub. No.: WO2015/118357
PCT Pub. Date: Aug. 13, 2015

(65) Prior Publication Data
US 2016/0348037 A1 Dec. 1, 2016

(30) Foreign Application Priority Data

Feb. 10, 2014 (GB) .................................. 1402257.8

(51) Int. Cl.
| | | |
|---|---|---|
| C11D 3/39 | (2006.01) | |
| C11D 3/20 | (2006.01) | |
| C11D 3/37 | (2006.01) | |
| C11D 11/00 | (2006.01) | |
| C11D 17/00 | (2006.01) | |
| A61K 8/02 | (2006.01) | |
| A61K 8/365 | (2006.01) | |
| A61K 8/73 | (2006.01) | |
| C11D 3/14 | (2006.01) | |
| C11D 3/22 | (2006.01) | |
| C11D 17/06 | (2006.01) | |
| A61K 8/44 | (2006.01) | |
| A61K 8/60 | (2006.01) | |
| A61Q 5/08 | (2006.01) | |
| A61Q 5/10 | (2006.01) | |
| A61Q 11/00 | (2006.01) | |
| A61Q 17/00 | (2006.01) | |
| C11D 3/33 | (2006.01) | |
| C11D 3/04 | (2006.01) | |
| A61K 8/49 | (2006.01) | |
| C11D 3/36 | (2006.01) | |
| A61K 8/38 | (2006.01) | |

(52) U.S. Cl.
CPC ............ *C11D 3/3945* (2013.01); *A61K 8/022* (2013.01); *A61K 8/365* (2013.01); *A61K 8/38* (2013.01); *A61K 8/44* (2013.01); *A61K 8/492* (2013.01); *A61K 8/60* (2013.01); *A61K 8/731* (2013.01); *A61K 8/732* (2013.01); *A61Q 5/08* (2013.01); *A61Q 5/10* (2013.01); *A61Q 11/00* (2013.01); *A61Q 17/005* (2013.01); *C11D 3/042* (2013.01); *C11D 3/14* (2013.01); *C11D 3/2075* (2013.01); *C11D 3/2086* (2013.01); *C11D 3/221* (2013.01); *C11D 3/222* (2013.01); *C11D 3/33* (2013.01); *C11D 3/362* (2013.01); *C11D 3/3753* (2013.01); *C11D 3/3761* (2013.01); *C11D 3/3776* (2013.01); *C11D 11/0011* (2013.01); *C11D 11/0064* (2013.01); *C11D 17/0013* (2013.01); *C11D 17/0039* (2013.01); *C11D 17/06* (2013.01)

(58) Field of Classification Search
None
See application file for complete search history.

(56) References Cited

U.S. PATENT DOCUMENTS

| | | | |
|---|---|---|---|
| 4,451,387 A | 5/1984 | Tai | |
| 5,091,106 A * | 2/1992 | Jacobs | C11D 3/3945 252/186.25 |
| 5,279,757 A | 1/1994 | Gethoffer et al. | |
| 5,480,577 A | 1/1996 | Nicholson et al. | |
| 5,929,015 A | 7/1999 | Lagnemo et al. | |
| 6,080,717 A * | 6/2000 | Hodgson | C12N 9/93 435/183 |
| 6,194,367 B1 | 2/2001 | Talley | |
| 6,391,845 B1 | 5/2002 | Speed et al. | |
| 6,878,680 B2 | 4/2005 | Kitko et al. | |

(Continued)

FOREIGN PATENT DOCUMENTS

| | | |
|---|---|---|
| CN | 1934237 | 3/2007 |
| EP | 0 200 163 A2 | 11/1986 |

(Continued)

OTHER PUBLICATIONS

Oct. 20, 2015 Search Report issued in International Patent Application No. PCT/GB2015/050364.

(Continued)

*Primary Examiner* — Joseph D Anthony
(74) *Attorney, Agent, or Firm* — Lucas & Mercanti, LLP

(57) ABSTRACT

A first aspect relates to a particle including: (a) at least one bleaching agent including an organic peroxyacid; (b) at least one component selected from: (i) saccharides and polysaccharides, and derivatives thereof; (ii) inorganic fillers selected from the group consisting of talcs, micas, zeolites, silicates, metal oxides and clays; and (iii) linear, branched and cross-linked polymers and copolymers; (c) at least one pH reducing agent; and (d) at least one chelating agent. Further aspects relate to a process for preparing the particle, a composition or a dough including the particle, and use of the particle in a cleaning composition, a dental care composition, a hair dyeing composition or decolouriser, an antimicrobial composition or a bleach composition.

15 Claims, No Drawings

(56) References Cited

U.S. PATENT DOCUMENTS

| | | |
|---|---|---|
| 2003/0176308 A1 | 9/2003 | Secemski et al. |
| 2005/0256016 A1 | 11/2005 | Oh et al. |
| 2006/0009367 A1 | 1/2006 | Gagliardi et al. |
| 2006/0122090 A1* | 6/2006 | Spanier .................. A01N 37/46 510/310 |
| 2006/0172909 A1 | 8/2006 | Schmiedel et al. |
| 2007/0032396 A1 | 2/2007 | Schmiedel et al. |
| 2007/0093402 A1* | 4/2007 | Assmann .............. C11D 3/3753 510/302 |
| 2007/0197419 A1 | 8/2007 | Bianchi et al. |
| 2008/0113893 A1 | 5/2008 | Rowland et al. |
| 2008/0200364 A1* | 8/2008 | Garaffa .................. C11D 3/221 510/488 |
| 2010/0081603 A1* | 4/2010 | Schmiedel ............ C11D 3/3719 510/302 |
| 2012/0028874 A1* | 2/2012 | Fernandez Prieto ........................ C11D 11/0088 510/375 |
| 2014/0057821 A1* | 2/2014 | Heppert ................. C11D 3/221 510/220 |

FOREIGN PATENT DOCUMENTS

| | | |
|---|---|---|
| EP | 0816481 | 1/1998 |
| EP | 0 852 259 A1 | 7/1998 |
| EP | 1 398 368 A1 | 3/2004 |
| EP | 1 482 026 A1 | 12/2004 |
| EP | 1 760 141 A1 | 3/2007 |
| GB | 2163175 A | 2/1986 |
| JP | 05043892 | 2/1993 |
| JP | 2001-524590 | 12/2001 |
| JP | 2006504809 | 2/2006 |
| JP | 2007536413 | 12/2007 |
| WO | 94/13773 A1 | 6/1994 |
| WO | 00/27960 A2 | 5/2000 |
| WO | 00/42158 A1 | 7/2000 |
| WO | 2004/081161 A1 | 9/2004 |
| WO | 2004/110613 A1 | 12/2004 |
| WO | 2005/090543 A1 | 9/2005 |
| WO | 2006/016179 A1 | 2/2006 |
| WO | 2008104546 A1 | 9/2008 |
| WO | 2008104547 A1 | 9/2008 |
| WO | 2009/050203 A1 | 4/2009 |
| WO | 2009/068569 A1 | 6/2009 |
| WO | 2009/068570 A1 | 6/2009 |
| WO | 2011/051681 A1 | 5/2011 |
| WO | 2012/066344 A1 | 5/2012 |
| WO | 2012/140438 A1 | 10/2012 |
| WO | 2012/140442 A1 | 10/2012 |
| WO | 2014/140550 A1 | 9/2014 |

OTHER PUBLICATIONS

Aug. 16, 2016 International Preliminary Report on Patentability issued in International Patent Application No. PCT/GB2015/050364.

Nov. 27, 2014 Search report issued in British Patent Application No. 1402257.8.

Examination Report dated Mar. 26, 2018, issued in Australian Patent Application No. 2015213848, 5 pages.

Office Action dated May 24, 2018, issued in Russian Patent Application No. 2016136356/04, 10 pages.

Office Action dated Aug. 28, 2018, issued in Chinese Patent Application No. 201580008053.0, 34 pages.

Office Action dated Jan. 8, 2019, issued in European Patent Application No. 15 703 833.2, 4 pages.

Office Action dated Mar. 5, 2019, issued in Japanese Patent Application No. 2016-550761, 10 pages.

Office Action dated Jun. 24 2019, issued in Indian Patent Application No. 201617026356, 8 pages.

* cited by examiner

PERACID-CONTAINING PARTICLE

The present invention relates to stable particles containing an organic peroxyacid, and methods for the preparation thereof. The invention further relates to compositions comprising said particles, and applications thereof, particularly in the field of cleaning products for domestic and industrial use.

BACKGROUND TO INVENTION

Bleaching agents are used in a plethora of cleaning applications in order to render stained materials uncoloured. Typically, bleaches are oxidising agents that act by the oxidation of conjugated or labile portions of a particular staining molecule. These bleaches are included in many cleaning formulations and are typically used in conjunction with other cleaning agents such as surfactants. A major use of these compounds is in laundry applications where bleaching can be required to give efficient stain removal, and in automatic dish washing (ADW) applications. A number of these bleaches are solid in nature, for example, metal salts of perborate or percarbonate, such as sodium perborate or sodium percarbonate (SPC). These materials are used in solid, powder formulations only as they can react rapidly with other components in liquid formulations, such as enzymes or fragrances, and can render these ineffectual, thereby reducing the bleaching efficiency of the overall formulation.

The persalts described above are typically used in conjunction with a bleach activator, such as tetraacetylethylenediamine (TAED) or sodium nonyloxybenzene sulfonate (SNOBS), which form peracid species upon degradation. These peracids can effectively bleach stains at lower temperatures than persalts. The use of these bleach activators also has the advantage of the bleaching formulation being able to bleach more hydrophobic stains; this is particularly true in the case of SNOBS.

There is growing demand from manufacturers and end users to prepare stable, efficacious bleaching agents and bleaching agent accelerators for use in hostile formulations such as powder, tablet, unit dose or liquid formulations. A key requirement in these cases is the ability to protect or stabilise the bleaching material from mutually reactive components in the formulation. In the case of laundry or automatic dish wash (ADW) detergents, the formulations are typically highly alkaline and can contain oxidatively labile species such as surfactants, enzymes or perfumes, all of which can be decomposed or denatured through the action of bleaches. Bleaches can also be susceptible to high pH of formulations, especially in liquid formulations, and particularly in the case of pre-formed peracids such as 6-phthalimidoperoxyhexanoic acid (PAP). PAP has been shown to possess particularly high bleaching efficacy in-use and can bleach stains, including hydrophobic stains, at lower temperatures than for a combination of SPC and TAED. However, PAP is sensitive to high pH, particularly in the presence of water or high humidity, and can decompose and oxidise sensitive ingredients in a laundry formulation, such as surfactants, enzymes or fragrances. As such, a number of methods have been developed to increase the stability of PAP in laundry applications.

WO2012/066344 (Reckitt and Coleman) describes the preparation of coated, dyed, particles composed of PAP in conjunction with a cellulosic or non-reducing saccharide binder with a polymeric disintegrant. The particles are prepared via extrusion/spheronisation or pelletisation and coated with a dye and a non-reducing sugar. The particles have applications in automatic dish wash applications where the non-reducing sugar coating eliminates discolouration of the dyed coating upon storage at 40° C. and 70% relative humidity.

US2006/0172909 (Henkel) describes the coating of a pre-formed percarboxylic acid, in particular PAP, with a multi layer coating comprising alternate anionic and cationic polymers to give a layer-by-layer coated material. These coated particles show increased stability in liquid detergent formulations when compared to the corresponding uncoated analogues.

WO200042158 (Proctor and Gamble) describes the preparation of bleaching agent or bleaching agent precursor particles containing a polymeric disintegrant, for use in laundry formulations. The particles are formed by a number of different processes including granulation, spray drying, extrusion and spheronisation. A critical part of the invention is the incorporation of the disintegrant which aids subsequent dissolution of the particle in the final wash medium.

U.S. Pat. No. 5,279,757 (Hoechst) describes peroxyacid-containing granules, in particular PAP, and their use in laundry applications. The granules are prepared by the wet granulation of PAP with linear polyacrylic acids in addition to anionic surfactants. The granules are then dried and coated with polyacrylic acid polymers or copolymers. The coated particles show increased storage stability in powder formats.

US2007093402 (Henkel) describes preparing a core of a peroxycarboxylic acid, preferably PAP, and at least partially coating the prepared core. The core formation is preferably carried out in the presence of polyvinyl alcohol (PVOH) and optionally an additional mineral, organic or polymeric acid.

WO2005090543 (Solvay) describes granular compositions of PAP containing polymeric or inorganic supports and preferably boric acid. These materials show improved stability at elevated temperature and relative humidity, as well as fast dissolution rates.

The present invention seeks to provide new formulations containing an organic peroxyacid bleaching agent. Pre-formed percarboxylic acids such as PAP are advantageous compared to other bleaching agents, such as persalts in combination with a bleach activator, as they are effective at lower temperatures, typically between 20 to 40° C., they do not require the addition of a stoichiometric quantity of a bleach activator, they can bleach hydrophobic stains and can provide antimicrobial benefits. However, it is well known that the lack of long term stability of the organic peroxyacid in liquid and highly alkaline formulations is a major disadvantage in the use of this group of products.

A key requirement for bleaching in cleaning applications, such as in laundry or ADW products, is the ability to prepare particles containing an organic peroxyacid which have long-term stability and which can withstand the highly alkaline environments of laundry or ADW formats, while not decomposing other ingredients in the formulation such as enzymes, perfumes or surfactants. Additionally, it is important that the particle must be able to dissolve efficiently and release the bleaching component into the cleaning medium.

PAP is also relatively dusty in nature and certain crystalline forms show poor dissolution in-use. There is therefore a requirement to obtain a stable, dust-free, easy to dissolve composition containing PAP which can be utilised in bleaching formulations.

STATEMENT OF INVENTION

The present applicant has found that incorporating a specific combination of components into an organic peroxyacid-containing particle can increase the stability of the particle.

More specifically, the present applicant has found that organic peroxyacids can be stabilised by formulating the material with a number of agents suitable for maintaining the pH of the peroxyacid, and which are able to facilitate the formation of an associated peroxyacid particle. Optionally, these particles can be subsequently coated with a responsive coating to further aid their stabilisation.

Thus, in a first aspect of the invention relates to a particle comprising:
(a) at least one bleaching agent comprising an organic peroxyacid;
(b) at least one component selected from:
  (i) saccharides and polysaccharides, and derivatives thereof;
  (ii) inorganic fillers selected from the group consisting of talcs, micas, zeolites, silicates, metal oxides and clays; and
  (iii) linear, branched and cross-linked polymers and copolymers;
(c) at least one pH reducing agent; and
(d) at least one chelating agent.

Advantageously, the presently claimed particles exhibit excellent stability and dissolve efficiently to release the bleaching component into the cleaning medium. A further advantage is the "processability" of the particles, in that they can be manufactured easily and cost effectively. The increased stability, ease of dissolution and ability to optionally further coat the particles results in robust particles that are reproducible and capable of withstanding small variations in the composition and purity of the raw materials.

A second aspect relates to a composition comprising a particle according to the invention.

A third aspect relates to the use of a particle according to the invention in a cleaning composition, a dental care composition, a hair dyeing composition or decolouriser, an antimicrobial composition or a bleach composition.

A fourth aspect relates to a process for preparing a particle according to the invention, said process comprising the steps of:
(1) forming a mixture of:
  (a) at least one bleaching agent comprising an organic peroxyacid;
  (b) at least one component selected from:
    (i) saccharides and polysaccharides, and derivatives thereof;
    (ii) inorganic fillers selected from the group consisting of talcs, micas, zeolites, silicates, metal oxides and clays; and
    (iii) linear, branched and cross-linked polymers and copolymers;
  (c) at least one pH reducing agent; and
  (d) at least one chelating agent;
  in a solvent;
(2) extruding the mixture obtained in step (1);
(3) processing the extruded mixture obtained in step (2) to form particles;
(4) drying the particles obtained in step (3); and
(5) optionally coating the particles obtained in step (4).

A fifth aspect relates to a dough comprising a particle according to the invention, and a solvent, preferably water.

A sixth aspect relates to a particle obtainable by or obtained by the process of the invention.

A seventh aspect of the invention relates to a particle comprising:
(a) at least one bleaching agent comprising an organic peroxyacid;
(b) at least one component selected from:
  (i) saccharides and polysaccharides, and derivatives thereof; and
  (ii) linear, branched and cross-linked polymers and copolymers;
(c) at least one component selected from:
  (i) a pH reducing agent; and
  (ii) a chelating agent.

An eighth aspect relates to a process for preparing a particle according to the invention, said process comprising the steps of:
(1) forming a mixture of:
  (a) at least one bleaching agent comprising an organic peroxyacid;
  (b) at least one component selected from:
    (i) saccharides and polysaccharides, and derivatives thereof; and
    (ii) linear, branched and cross-linked polymers and copolymers;
  (c) at least one component selected from:
    (i) a pH reducing agent; and
    (ii) a chelating agent;
  in a solvent;
(2) extruding the mixture obtained in step (1);
(3) processing the extruded mixture obtained in step (2) to form particles;
(4) drying the particles obtained in step (3); and
(5) optionally coating the particles obtained in step (4).

DETAILED DESCRIPTION

The present invention relates to particles containing an organic peroxyacid active (e.g. PAP). These particles can be subsequently coated to provide increased protection for the organic peroxyacid active and can be used in laundry detergents and cleaning compositions, especially in solid or liquid laundry detergents and cleaning compositions. In addition they can also be utilised in dental care compositions, hair dyeing compositions and decolouriser or antimicrobial or bleach compositions for industrial applications. The particles or coated particles can be admixed in with liquid or solid formats, used as powders, slurries, liquids or compressed tablets, or can be used in single or multi-compartment unit dose formats, especially in cleaning applications such as laundry detergents or automatic dish wash (ADW) formulations.

Preferably, the particles of the invention are boron-free. This is due to the high ecotoxicology of boron-containing materials and since the majority or PAP-containing bleaches then it is desirable to have little or no boron-containing materials within a formulation. As used herein, the term "boron-free" refers to a particle having substantially no boron present in its composition, and preferably less than about 1000 ppm (or 0.1% w/w), more preferably, less than about 500 ppm (or 0.05% w/w) by weight of the particle. In one particularly preferred embodiment, the particle contains less than about 100 ppm (or 0.01% w/w) boron.

As used herein, the term "particle" encompasses the singular and plural.

In one preferred embodiment, the particle has a particle size of from about 10 to about 10,000 µm. The particles can be spherical, or spheroidal, or cylindrical in shape. Where the particles are spherical, or spheroidal, their preferred mean particle diameters are from about 10 to about 3,000 μm, more preferably from about 100 to about 2,000 μm. Where the particles are cylindrical in shape, preferably they have mean diameters of from about 100 μm to about 2,000 μm. Preferably, the cylinders are of about 0.5 to about 5 cm in length.

In one particularly preferred embodiment, the particle is spheroidal.

Filler/Binder

The particles of the invention preferably contain a component which is a filler or binder material.

A key requirement for the binder material is that, in solvent-based extrusion and spheronisation, where the materials are mixed with a solvent and subsequently dried after particle formation or coating, the filler or binder material dissolves or swells in the solvent. In the case where the extrusion is via a thermal route, it is preferred that the binder or filler can soften or melt at the processing temperatures used. Another requirement for the binder or filler is that it does not contain components or moieties which can accelerate the decomposition of the active compound, (e.g. PAP), such as amine groups, transition metals or salts thereof, halogens or halogen anions, Brönsted or Lewis bases.

In one preferred embodiment, the filler is inert to the action of the active compound, or can increase the stability of the active, for example, by lowering the pH of the immediate environment or coating the material during processing. During the solvent-based processing of the material a common solvent used is water. As such, it is preferable that the filler can swell, or partially or fully dissolve in water and give effective mechanical binding of the components during the processing of the particle. This ability to swell or partially or fully dissolve in water is also beneficial during the extrusion step as the bound water or filler solution can aid in the lubrication of the wet mass through the apertures in an extruder system. The extruded wet mass will then have the necessary mechanical properties to form a coherent extrudate which can hold together and be further shaped or processed. The filler can also help in the break-up and final dissolution by swelling or dissolving in the aqueous formulation and thus helping the final dissolution of the PAP-containing particle.

The filler is preferably present in amounts ranging from about 0 to about 40%, more preferably about 1 to about 40, more preferably about 1 to about 20%, by weight relative to the total weight of the particle. In another preferred embodiment, the filler is present in an amount of from about 5 to about 25%, more preferably from about 5 to about 15%, or about 5 to about 10% by weight relative to the total weight of the particle.

The filler/binder is selected from:
(i) saccharides and polysaccharides, and derivatives thereof;
(ii) inorganic fillers selected from the group consisting of talcs, micas, zeolites, silicates, metal oxides and clays; and
(iii) linear, branched and cross-linked polymers and copolymers.

In one preferred embodiment, the filler is a saccharide. As used herein, the term "saccharide" refers to the group that includes sugars, starch and cellulose. The saccharides are divided into the following chemical groups: monosaccharides, disaccharides, oligosaccharides and polysaccharides.

As used herein, the term "monosaccharide" refers to the simple sugars that are the building blocks of carbohydrates. A monosaccharide cannot be further reduced by hydrolysis into another simple sugar. Examples of monosaccharides include glucose (dextrose), fructose (levulose) and galactose.

As used herein, the term "disaccharide" refers to a carbohydrate formed when two monosaccharides undergo a condensation reaction which involves the elimination of a small molecule, such as water. Examples of disaccharides include sucrose, lactose, and maltose.

As used herein, the term "oligosaccharide" refers to a carbohydrate formed from a small number (typically three to nine) of monosaccharide units.

As used herein, the term "polysaccharide" refers to polymeric carbohydrate molecules composed of long chains of monosaccharide units bound together by glycosidic linkages, which on hydrolysis give the constituent monosaccharides or oligosaccharides. Polysaccharides range in structure from linear to highly branched. The term "polysaccharide" typically refers to molecules containing ten or more monosaccharide units, although it may also encompass molecules with fewer than ten monosaccharide units. When all the monosaccharides in a polysaccharide are the same type, the polysaccharide is called a homopolysaccharide or homoglycan, but when more than one type of monosaccharide is present they are called heteropolysaccharides or heteroglycans.

Polysaccharides have the general formula of $C_x(H_2O)_y$, where x is typically a number between 200 and 2500. As the repeating units in the polymer backbone are often six-carbon monosaccharides, the general formula can also be represented as $(C_6H_{10}O_5)_n$ where $40 \leq n \leq 3000$. Examples of suitable polysaccharides include starch, cellulose, glycogen, chitin, callose or laminarin, chrysolaminarin, xylan, arabinoxylan, mannan, fucoidan and galactomannan.

In one preferred embodiment, the filler is a monosaccharide, a disaccharide or a polysaccharide.

As used herein, the term "derivative" refers to a chemically or physically modified saccharide or polysaccharide, for example, carboxy methyl cellulose.

In one preferred embodiment, the filler is a polysaccharide. Preferably, the polysaccharide is selected from: cellulose and derivatives thereof, cellulose fibres, more preferably microcrystalline cellulose (such as the Avicel® range from FMC), methyl cellulose, hydroxyethyl cellulose, hydroxypropyl cellulose or carboxy-functional celluloses such as carboxymethyl cellulose;

natural gums, preferably guar, locus bean, zien gum and gum shellac, acacia gum carageenan, pectins, chitosan or emcosoy; and starches and modified starches, preferably pregellatinised starches or variants thereof.

In one particularly preferred embodiment, the filler is a starch. Starches are glucose polymers in which glucopyranose units are bonded by alpha-linkages. More preferably, the filler is a starch selected from potato starch, maize starch, wheat starch, rice starch and partially pregellatinised maize starch.

In one particularly preferred embodiment, the filler is potato starch, preferably pregellatinised potato starch.

In one preferred embodiment, the filler is a monosaccharide.

In another preferred embodiment, the filler is a disaccharide.

In another preferred embodiment, the filler is a trisaccharide.

In another preferred embodiment, the filler is an oligosaccharide.

In one preferred embodiment, the filler is a non-reducing sugar selected from sucrose, mannitol, isomalt, xylitol, sorbitol, trehalose and lactitol.

In one preferred embodiment, the filler is a linear, branched or cross-linked polymer or copolymer, or a mixture thereof, selected from polyvinylpyrrolidone, a functionalised poly(vinyl) alcohol, a linear, branched or cross-linked polymer or copolymer prepared from one or more of the following monomers: N-vinylpyrollidone, (meth)acrylic acid, acrylic acid, maleic acid, fumaric acid, itaconic acid, 2-acrylamido-2-methyl-1-propanesulfonic acid, vinyl alcohol and vinyl acetate; functionalised poly (vinyl alcohol)s, such as acetals, for example, butyl acetals, polymers such as Kolloidon® or Luvicross® from BASF, commercially available acrylic copolymers such as the Carbopol® (homo- and copolymers of acrylic acid crosslinked with a polyalkenyl polyether) or Ultralez 10, 21, 30 or Noveon®AA-1 range from Lubrizol (acrylic acid polymer crosslinked with divinyl glycol), the Sokolan® range from BASF (PAA) such as CP5, CP10 and PA30.

In one highly preferred embodiment, the filler is selected from polyvinylpyrrolidone, polyacrylic acid, poly(meth) acrylic acid and cross-linked polyacrylic acid.

In one preferred embodiment, the filler comprises a mixture of a linear, branched or cross-linked polymer or copolymer, and a saccharide or polysaccharide, or a derivative thereof.

In one preferred embodiment, the filler comprises an inorganic filler selected from the group consisting of talcs, micas, zeolites, silicates, metal oxides and clays.

In one preferred embodiment, the filler comprises a mixture of a linear, branched or cross-linked polymer or copolymer, and an inorganic filler selected from the group consisting of talcs, micas, zeolites, silicates, metal oxides and clays.

Preferred metal oxides include magnesium and aluminium oxides. Preferred clays include bentonite, functionalised bentonites, lapponite, montmorrillonite, kaolin and synthetic magnesium aluminosilicates.

Chelating Agent

It is known that the presence of transition metals can accelerate the decomposition of peroxides and peracids. Accordingly, in one preferred embodiment, a metal chelating agent, that is a compound which is known to chelate or ligate transition metal salts, is included in the particle of the present invention.

In one preferred embodiment, the chelating agent is selected from ethylenediaminetetraacetic acid (EDTA), glutamic acid diacetic acid (GLDA), diethylene triamine pentaacetic acid (DTPA), hydroxyethylethylenediaminetriacetic acid (HEDTA), nitrilotriacetic acid (NTA), ethanoldiglycinic acid (EDG), 2,2',2'',2'''-(1,2-propanediyldinitrilo)tetraacetic acid (PDTA), glucoheptonate, N,N-bis(carboxymethyl)-L-glutamic acid, nitroacetic acid, phosphoric acid and polymers of phosphoric acid, aminopolyphosphonic acid, 1-hydroxy-ethylene-1,1-diphosphoric acid (HEDP), diethylenetrianime penta(methylenephosphonic acid) (DTPMP), azacycloheptane diphosphonate (AHP), 1-hydroxyethylidene-1,1-diphosphonic acid, diethylenetriamine penta(methylene phosphonic acid), polyamino phosphonic acid, bis(hexamethylene triamine penta(methylenephosphonic acid)), the sodium salt of diethylene triamine penta (methylene phosphonic acid), 2-phosphonobutane-1,2,4-tricarboxylic acid and amino tri(methylene phosphonic acid (ATMP).

In some instances, where the chelating agent is an acidic agent, it can also serve to reduce the pH in a similar manner to the pH reducing agent. In these instances, where the chelating agent is an acidic agent, the particle may contain a lower amount of the pH reducing agent. In one alternative embodiment, where the chelating agent is an acidic agent, the pH reducer may be absent altogether, i.e. the chelating agent has a dual functionality and can also function as a pH reducer.

The chelating agent is preferably present in amounts ranging from about 0.01 to about 20%, more preferably about 0.1 to about 10%, by weight relative to the total weight of the particle. In one preferred embodiment, the chelating agent is present in an amount of from about 0.5 to about 2.0%, more preferably from about 0.5 to about 1.0%, more preferably from about 0.6 to about 0.8% by weight relative to the total weight of the particle. In embodiments of the invention where no pH reducing agent is present, larger amounts of chelating agent may be included, e.g. up to about 5% by weight relative to the total weight of the particle.

pH Modifying Agent

In order to form robust and formulation-stable particles, the choice of adducts in the particle is an important one. Organic peroxyacids such as PAP are most stable in an acidic environment, preferably having a pH of less than about 6.5, and more preferably from about 6 to about 2. Accordingly, the presently claimed particles preferably contain a 15 pH modifying agent which is a pH reducing agent.

Preferably, the pH reducing agent is an acidifying agent that is capable of lowering the pH to provide an acidic medium. pH measures how acidic a solution is. Preferably, the pH reducing agent has a pH in aqueous solution of less than about 7, more preferably, less than about 6.

In one preferred embodiment, the acidifying agent has a pKa of less than about 7, more preferably, a pKa of less than about 6. pKa is the dissociation constant of a particular hydrogen atom in a molecule and measures how acidic (or not) a given hydrogen atom in a molecule is.

In one preferred embodiment, the pH reducing agent is an inorganic, organic or polymeric acid.

In one preferred embodiment, the pH reducing agent is selected from citric acid, tartaric acid, tartronic acid, malonic acid, oxalic acid, maleic acid, itaconic acid, malonic acid, fumaric acid, hydrochloric acid, sulfuric acid, phosphoric acid, gluconic acid, lactic acid, toluene sulfonic acid, ascorbic acid, acetic acid and methane sulfonic acid. Additionally compounds which can further react, such as via hydrolysis, to give acidic moieties such as cyclic lactams or lactones such as δ-gluconolacone can be used.

Preferred polymeric acids include linear, branched or cross-linked polymers and copolymers of acrylic acid, methacrylic acid, maleic acid, fumaric acid, itaconic acid, styrene sulfonic acid, vinyl benzoic acid, 2-acrylamido-2-methyl-1-propanesulfonic acid and dimethylolpropionic acid.

Due to the harmful nature of boronic acids, these materials are preferably to be avoided in the preparation of peroxyacid-containing particles.

The pH reducing agent is preferably present in an amount ranging from about 0.1 to about 30%, more preferably about 1 to about 20%, by weight relative to the total weight of the particle. In one preferred embodiment, the pH reducing agent is present in an amount of from about 1 to about 10%, more preferably from about 1 to about 6%, even more preferably, from about 2 to about 3% by weight relative to the total weight of the particle.

Bleaching Agent

In one preferred embodiment, the bleaching agent is a compound of formula (A.1) or (B.1):

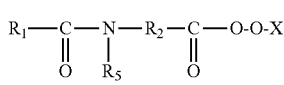 (A.1)

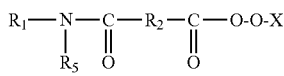 (B.1)

wherein:
$R_1$ is a $C_{1-16}$-alkyl, $C_{2-16}$-alkenyl, $C_{3-16}$-cycloalkyl, $C_{6-12}$-aryl or $C_{1-16}$-alkyl-$C_{6-12}$-aryl group; $R_2$ is a $C_{1-16}$-alkylene, $C_{3-16}$-cycloalkylene or $C_{6-12}$-arylene group; $R_5$ is H, or a $C_{1-16}$-alkyl, $C_{2-16}$-alkenyl, $C_{3-16}$-cycloalkyl, $C_{6-12}$-aryl or $C_{1-16}$-alkyl-$C_{6-12}$-aryl group; or $R_5$ is linked to $R_1$ (preferably via a carbonyl group) to form a cyclic group; and X is selected from H, an alkali metal cation, an alkaline earth metal cation, an ammonium cation and an alkylammonium cation.

In one preferred embodiment, the bleaching agent is a compound of formula (A.2), where Y is a linear or branched, substituted or un-substituted hydrocarbon chain having from 1 to 8 carbons

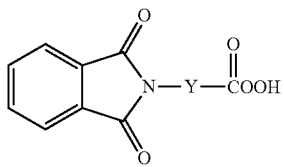 (A.2)

In one preferred embodiment, the bleaching agent is selected from: diperoxyalkanedioc acids having 6 or more carbon atoms, preferably diperoxydodecanedioc acid (DPDA), diperoxytetradecanedioc acid and diperoxyhexadecanedioc acid; mono- and diperazelaic acid, mono- and diperbrassylic acid, 6-phthalimidoperoxyhexanoic acid (PAP), nonanoylamido peroxo-adipic acid (NAPAA) and hexane sulfenoyl peroxypropionic acid.

In one highly preferred embodiment, the bleaching agent is 6-phthalimido-peroxy-hexanoic acid (PAP).

In one preferred embodiment, the bleaching agent is present in an amount of from about 20 to about 95%, more preferably about 40 to about 85%, by weight relative to the total weight of the particle. In one preferred embodiment of the invention, the bleaching agent is present in an amount of from about 40 to about 90%, more preferably about 40 to about 80%, even more preferably from about 45 to about 80% by weight relative to the total weight of the particle. In another preferred embodiment, the particle comprises at least 45%, preferably at least 50%, even more preferably, at least 55% of the bleaching agent by weight relative to the total weight of the particle.

In one particularly preferred embodiment, the bleaching agent is a commercially available bleaching agent, such as PAP, for example those sold under the trade names Eureco WM1 or Eureco MG, available from Solvay. Typically, the bleaching agent (PAP) is present in an amount of about 70% by weight in such commercially available formulations.

Accordingly, in another preferred embodiment of the invention, the commercially available bleaching agent such as Eureco WM1 or Eureco MG is present in an amount of from about 60 to about 90%, more preferably about 40 to about 80%, even more preferably from about 45 to about 80% by weight relative to the total weight of the particle. In another preferred embodiment, the particle comprises at least 70%, preferably at least 75%, even more preferably, at least 80% of the commercially available bleaching agent by weight relative to the total weight of the particle.

Additional Excipients

In one preferred embodiment, the particle further comprises a surfactant, more preferably a non oxidizable surfactant.

Preferably, the non-oxidizable surfactant is an anionic or non-ionic surfactant.

Surfactants are also an important material within the active-containing particle. Surfactants act by lubricating the mechanical processes during the particle formation such as extrusion and spheronisation and also helping to bind the components together. It is important that the surfactant does not react with the active component, e.g. PAP, and as such, it is preferred that the surfactant is a non-oxidisable surfactant, as other materials may reduce the active content of the bleach upon storage.

The surfactant or surfactants, potentially in combination with the filler, can also aid in the formation of a coherent and mechanically stable extrudate which is deformable and can be further shaped such as via spheronisation. The surfactant can also help in the dissolution of the formed particle and can aid in the dissolution of the final particle by increasing the propensity of water diffusion and break-up of the particle in the final wash solution.

Suitable surfactants include non oxidisable species including but not limited to non-ionic and anionic surfactants including non-ionic surfactants such as linear or branched primary $C_6$ to $C_{18}$ alkyl ethoxylates such as the Unithox® range from Baker Hughes. It is particularly preferable to use anionic surfactants such as sodium, potassium, ammonium and substituted ammonium salts of linear or branched alkyl or aryl primary or substituted sulfates, sulfonates, phosphonates, sarcosinates or carboxylates. Anionic sulfates are particularly preferred and preferred examples include linear and branched primary and secondary alkyl sulfates, alkylethoxy sulfates, fatty oleoyl glycerol sulfates and alkyl phenol ethylene oxide ether sulfates.

In one preferred embodiment, the surfactant is an alkyl sulfate, preferably a linear or branched primary $C_{10}$ to $C_{18}$ alkyl sulfate, more preferably a $C_1$, to $C_{14}$ linear or branched alkyl sulfate. Anionic sulfonate surfactants can also be used such as the aforementioned salts of $C_5$ to $C_{20}$ linear or branched alkylbenzene sulfonates, and in particular, $C_9$ to $C_{14}$ linear or branched alkylbenzene sulfonates. Preferred examples include linear alkyl benzene sulfonate (LAS), sodium laureth and sodium myreth sulfates. Commercial anionic surfactants such as the Hostapur® range from Clariant such as SAS 30, 60 or 93 can also be used. Hostapur SAS is a secondary alkyl sulfonate having the structure shown below:

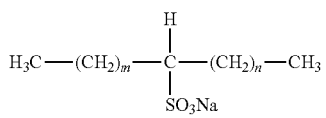

where m and n=11-14.

The sulfonate group is distributed over the carbon chain in such a way that it is mainly the secondary carbon atoms that are substituted.

In one preferred embodiment, the surfactant is selected from sodium $C_{14}$ to $C_{17}$ sec alkyl sulfonate and a linear or branched primary $C_6$ to $C_{18}$ alkyl ethoxylate.

In one preferred embodiment, the non-oxidizable surfactant is selected from secondary alkane sulfonates, ethoxylated alkanes, ethoxylated aromatics, fatty acids, preferably, stearic acid, palmitic acid, myristic acid and metal soaps thereof.

Preferably, the surfactant is present in an amount of from about 0 to about 30%, more preferably about 1 to about 30%, more preferably about 1 to about 20%, by weight relative to the total weight of the particle. In one preferred embodiment, the surfactant is present in an amount of from about 1 to about 12%, more preferably from about 2 to about 10%, even more preferably from about 3 to about 8% by weight relative to the total dry weight of the particle.

In one preferred embodiment, the particle further comprises a dye or a pigment. The particle can be coloured for aesthetic enhancement and this can be achieved by the incorporation of a coloured dye or pigment into the core of the particle, or in the coating.

Pigments are particularly preferred as they are less susceptible to bleaching by the active PAP agent. Additionally, these materials are more suitable for use in laundry formulations as they give less spotting of fabrics. The pigments can be inorganic or organic in nature and can be used in their native crystalline form or coated or absorbed with or onto an inert material.

PREFERRED EMBODIMENTS

In one preferred embodiment, the particle of the invention is in the form of a spheronised particle.

In another preferred embodiment, the particle of the invention is in the form of an extrudate which is then divided or chopped into smaller segments, for example, resembling chopped noodles.

Further details of the preparation are set out below.

In one preferred embodiment, the particle of the invention comprises:
(a) at least one bleaching agent comprising an organic peroxyacid;
(b) at least one component selected from:
  (i) saccharides and polysaccharides, and derivatives thereof; and
  (ii) linear, branched and cross-linked polymers and copolymers;
(c) at least one pH reducing agent; and
(d) at least one chelating agent.

In one preferred embodiment, the particle of the invention comprises:
(a) at least one bleaching agent comprising an organic peroxyacid;
(b) at least one component selected from:
  (i) saccharides and polysaccharides, and derivatives thereof; and
  (ii) linear, branched and cross-linked polymers and copolymers;
(c) at least one pH reducing agent;
(d) at least one chelating agent; and
(e) at least one non-oxidizable surfactant.

In one preferred embodiment, the particle of the invention comprises:
(a) at least one bleaching agent comprising an organic peroxyacid;
(b) at least one component selected from saccharides and polysaccharides, and derivatives thereof; and
(c) at least one pH reducing agent;
(d) at least one chelating agent; and
(e) optionally at least one non-oxidizable surfactant.

In one preferred embodiment, the particle of the invention comprises:
(a) at least one bleaching agent comprising an organic peroxyacid;
(b)(i) at least one component selected from saccharides and polysaccharides, and derivatives thereof; and
(b)(ii) at least one component selected from linear, branched and cross-linked polymers and copolymers;
(c) at least one pH reducing agent; and
(d) at least one chelating agent.

Highly preferred embodiments of the invention are set forth in the accompanying non-limiting examples. Particularly preferred examples are formulations S11-S15.

Compositions and Applications Thereof

Another aspect of the invention relates to a composition comprising a particle as described above.

In one preferred embodiment, the composition is a laundry detergent, an auto-dishwasher product or a cleaning composition. The skilled person would be familiar with the components of such compositions.

In one particularly preferred embodiment, the composition is a solid.

In another particularly preferred embodiment, the composition is a liquid.

Another aspect of the invention relates to the use of a particle as described above in a cleaning composition, a dental care composition, a hair dyeing composition or decolouriser, an antimicrobial composition or a bleach composition.

Dough

Another aspect of the invention relates to a dough comprising a particle as described above and a solvent, preferably an aqueous solvent, more preferably water. Thus, in one highly preferred embodiment, the invention relates to an aqueous dough. Preferably, the aqueous dough comprises a residual amount of water, more preferably, 5% or less w/w, even more preferably 4% or less w/w after processing.

Process for Preparing Particles

Another aspect of the invention relates to a process for preparing a particle as described above, said process comprising the steps of:
(1) forming a mixture of:
  (a) at least one bleaching agent comprising an organic peroxyacid;
  (b) at least one component selected from:
    (i) saccharides and polysaccharides, and derivatives thereof;
    (ii) inorganic fillers selected from the group consisting of talcs, micas, zeolites, silicates, metal oxides and clays; and
    (iii) linear, branched and cross-linked polymers and copolymers;
  (c) at least one pH reducing agent; and
  (d) at least one chelating agent;
  in a solvent;
(2) extruding the mixture obtained in step (1);
(3) processing the extruded mixture obtained in step (2) to form particles;
(4) drying the particles obtained in step (3); and
(5) optionally coating the particles obtained in step (4).

Another aspect of the invention relates to a process for preparing a particle as described above, said process comprising the steps of:
(1) forming a mixture of:
  (a) at least one bleaching agent comprising an organic peroxyacid;
  (b) at least one component selected from:
    (i) saccharides and polysaccharides, and derivatives thereof; and
    (ii) linear, branched and cross-linked polymers and copolymers;
  (c) at least one component selected from:
    (i) a pH reducing agent; and
    (ii) a chelating agent;
  in a solvent;
(2) extruding the mixture obtained in step (1);
(3) processing the extruded mixture obtained in step (2) to form particles;
(4) drying the particles obtained in step (3); and
(5) optionally coating the particles obtained in step (4).

In one preferred embodiment, the solvent is an aqueous solvent, preferably water.

The particles can be prepared by various agglomeration techniques including; spray drying, wet or spray granulation, extrusion and Marumerisation or spheronisation. Preferred methods are those which can produce a compact particle and where other agents can be added to increase the stability or dissolution of the final particle. Extrusion of a melt, paste or slurry of the ingredients is particularly preferred. In this case the ingredients are pre-mixed and heated to soften the mixture or an inert solvent is added and the plasticised mass extruded through a circular or shaped die, with heating in the case for the molten mixture.

Following extrusion the extruded "noodles" can be further processed such as via chopping to form "chopped noodles or needles" to give cylindrical particles where the die is circular or shaped "noodles" where the die is non-circular. The formed particles can be subsequently cooled or dried to give coherent particles.

In one preferred embodiment, step (3) comprises a spheronisation step or manual chopping step, with a mechanical cutter blade either fitted after the extrusion plate or through a separate mechanically-driven cutting process.

In one highly preferred embodiment, the process comprises breaking a pre-formed extrudate to form a spheronised particle. Spheronisation, or Marumerisation, is a process whereby a pre-formed cylindrical extrudate, formed from a deformable molten or solvent-associated or swollen paste, is converted to a spherical or spheroidal particle by the action of a rapidly spinning, indented disc positioned at the bottom of a shaped bowl. The extruded particles break-up on the spinning disk and via a combination of rolling and roping form uniform spherical or spheroidal particles proportional to the original diameter of the cylindrical extrudate. Spheroids have the advantage of being uniform in shape and size distribution and are typically cooled or dried after preparation in order to provide coherent particles or cores. Additionally, spheroids have the advantage of possessing a higher density shell around the formulation which can afford additional mechanical or chemical protection to the actives.

In a typical process the PAP and other ingredients are mixed in a conventional powder/liquid mixed such as a Loedige KM mixer at an industrial scale or a conventional food mixer such as a Kenwood FPP220 Multipro Compact at a laboratory scale. In the case of the solvent-borne process it is preferred that this mixing takes place at room temperature with the addition of water to moisten the dough and form a deformable mass. The extrusion of the wet mass can be performed in any conventional extruder geometry such as axial, radial or dome-like or a combination such; examples of extruders would be a Fuji Paudal QJ-1000 for an industrial scale or a Caleva 250 for use at a laboratory. It is preferable that the orifice diameter in the extruders should be in the range of from about 0.1 to about 5 mm, and more preferably from about 0.5 to about 3 mm.

Particle formation can also be performed by cutting or chopping of the extrudate, for example by the use of a rotational cutting blade fitted to the end of the orifice plate or by rollering or moulding the extrudated noodles.

In one preferred embodiment, step (3) comprises a wet-moulding process.

Solvents are used in the wet-route to prepare particles where they are used to swell or dissolve the binders or fillers and provide plasticity to the dough during particle formation, such as via extrusion. Preferred solvents are non-reactive with the PAP active and are non-flammable and non toxic. A particularly preferred solvent is water. Solvents should be present at levels of from about 0 to about 40%, more preferably about 5 to about 25%.

Where the particles have been formed by a wet process, typically using water as the solvent, the particles can dried by a fluid bed drying process such as by using a Glatt Mini Glatt fluidised bed drier.

In one embodiment, the whole particle formation process can therefore be thought of as:
1. Mixing of the ingredients in combination with a quantity of water to form a wet mass.
2. Extrusion of the wet mass to form "noodles".
3. Shaping of the noodles either by chopping or spheronisation or a similar rolling or moulding process
4. Drying of the noodles or shaped particles such as via a fluid bed drier.
5. Optionally coating the formed cores.

In one preferred embodiment, step (5) comprises coating the particles with a coating material in a fluid bed drier.

Another aspect of the invention relates to a particle obtainable by or obtained by the process as described above.

Coatings

In one preferred embodiment, the particle comprises at least one coating layer.

In one preferred embodiment, the coating layer comprises an inorganic coating, preferably selected from sodium sulfate, monosodium citrate, sodium diphosphate and magnesium sulfate.

In one preferred embodiment, the coating layer comprises a polymer selected from polyvinyl alcohol, polyvinyl butyral (PVB), a polyolefin, and an amphiphilic graft copolymer, and mixtures of two or more thereof. In one highly preferred embodiment, the coating layer comprises a polyvinyl alcohol such as Molwiol® (Kuraray Chemical Co; various grades available). In one highly preferred embodiment, the coating layer comprises functionalised PVOH, e.g. butyrated PVOH (butyrated Molwiol®). Preferably, the coating layer comprises PVOH functionalised with 1-30% butyraldehyde, more preferably, 5-20% butyraldehyde.

In one preferred embodiment, the coating layer comprises a polymer, a wax, or a mixture thereof, more preferably a pH-responsive polymer or a siloxane-based polymer.

As used herein the term "responsive polymer" refers to a polymer that retains its structural integrity within the product format (formulation), but which responds to a particular trigger, for example, a change in pH, temperature, ionic concentration or the like. Preferably, the responsive polymer is a pH-responsive polymer.

Suitable responsive polymers include, but are not limited to, those based on poly(ethylene glycol), a weakly basic, or weakly acidic polymer such as a copolymer or (meth)acrylic acid or dimethylaminoethyl (meth)acrylate or polyvinyl alcohol mentioned above, and which change in their physical form, for example their solubility of hydrophilicity or hydrophobicity in response to a trigger stimulus which may take the form of a change in pH, of temperature, of ionic strength or of dilution. By way of example, suitable pH-responsive polymers for the coating layer are described in WO 2012/140438 (Revolymer Limited). Suitable ionic-strength responsive polymers for the coating layer are described in WO 2012/140442 (Revolymer Limited). Other suitable polymers for the coating layer are described in WO 2011/051681 (Revolymer Limited).

In one preferred embodiment, the coating comprises an amphiphilic polymer, more preferably an amphiphilic graft copolymer. Suitable amphiphilic graft copolymers are described in WO 2009/068569, WO 2009/050203 and WO 2009/068570, all in the name of Revolymer. Further details on amphiphilic polymers are set out hereinbelow.

In one preferred embodiment, the coating may optionally comprise other materials and/or layers which fulfil functions such as provision of primer layer(s) or filler(s) or other material(s) which provide(s) a particular function not necessarily related to providing a response to stimulus or stimuli. For example, extra layers may be required to provide an inter-layer or core-layer adhesive effect or may simply be binders, fillers, coloured materials or primers.

In one preferred embodiment, the additional layer is a primer layer, a filler layer, an anticaking agent or flow aid incorporated as a layer or an adhesion promoting layer, or a combination thereof.

For example, further optional layers may comprise materials whose function is to provide a primer layer or layers in order to give greater compatibility and/or adhesion between chemically dissimilar layers. Primer layers may be applied at any level within the layers and may be directly applied to or within the particle core. Further optional layers may be present such as filler materials or anticaking/anti-adhesion agents which may be inorganic or organic in chemical nature and may be present in a functionally neutral capacity (e.g. non-responsive to external stimuli) so as to adjust, as non-limiting examples, the density or the correct ratio of components within the composite particle.

Waxes

In one preferred embodiment, the coating comprises a blend of a wax or wax-like substance and an amphiphilic copolymer. Suitable examples of such blends are described in GB1304667.7 (which published as WO 2014/140550; Revolymer). The term "wax or wax-like substance" refers to a material which is composed primarily of hydrocarbon groups such as a polymer formed from the polymerisation of alpha-olefins, but may also refer to a natural wax which may contain various types of chemical functionality depending on the source and the natural processes involved in its production. It should be noted that whilst natural waxes contain varied chemical functionality, in general, the degree of functionalisation is not sufficient to make the wax responsive in the manner which is described herein in respect of the amphiphilic polymer.

In essence the wax or wax-like substance is a material which is waterproof. This material may preferably be described as a wax, that is to say a material that has some plasticity at normal ambient temperatures and a melting point of above around 30° C. A single wax may be used or a blend of two or more different waxes may be used in the composite.

Waxes are organic compounds that characteristically consist of long alkyl chains. The wax may be a natural wax or a synthetic wax. Natural waxes are typically esters of fatty acids and long chain alcohols. Terpenes and terpene derivatives may also be described as natural waxes. Synthetic waxes are typically long-chain hydrocarbons lacking functional groups.

In one preferred embodiment, the wax is a petroleum wax. Petroleum waxes include, but are not limited to, the following: paraffin waxes (made of long-chain alkane hydrocarbons), microcrystalline waxes (e.g. with very fine crystalline structure), and petroleum jelly. For example, the Bareco Baker Hughes family of microcrystalline waxes are petroleum-derived microcrystalline waxes consisting of complex mixtures of paraffinic, isoparaffinic, and naphthenic hydrocarbons.

Paraffin waxes represent a significant fraction of petroleum and are refined by vacuum distillation. Paraffin waxes are typically mixtures of saturated n- and iso-alkanes, naphthenes, and alkyl- and naphthene-substituted aromatic compounds. The degree of branching has an important influence on the properties.

Other synthetic waxes include, but are not limited to, polyethylene waxes (based on polyethylene), Fischer-Tropsch waxes, chemically modified waxes (for example, esterified or saponified), substituted amide waxes, and polymerized α-olefins. Some waxes are obtained by cracking polyethylene at 400° C. The products have the formula $(CH_2)_nH_2$, where n ranges between about 50 and 100. Additionally synthetic waxes may contain chemical functionalisation such as the carboxylated wax VYBAR C6112 produced by Baker Hughes from which it is possible to produce other further functionalisation such as pegylation, by reaction with a suitable mono-, di-, or polyhydric alcohol or alkoxylated akso possible, for example, silylation, siliconylisation and the like.

Examples of suitable naturally occurring materials include beeswax, candelilla wax, carnauba wax, paraffin wax, ozokerite wax, ceresine wax, montan wax. Synthetic waxes are also available and examples in this class include microcrystalline waxes such as the Bareco™ range of microcrystalline waxes; the VYBAR™ range of highly branched polymers derived from the polymerisation of alpha olefins; the PETROLITE™ range of polymers and the POLYWAX™ range of polyethylenes.

In one highly preferred embodiment, the wax or wax-like material is selected from the VYBAR™ (Baker Hughes) range of highly branched polymers derived from the polymerisation of alpha olefins and may be a single product chosen from the range or a mixture of two or more products in the range. Particularly preferred is the highly branched synthetic wax VYBAR 260™.

Blends of two or more natural waxes, or two or more synthetic waxes, or blends of one or more natural waxes and one or more synthetic waxes or blends of chemically functionalised synthetic waxes with other synthetic or natural waxes are also suitable for use in the present invention. As will be appreciated by those skilled in the art, such blends can be used to blend the properties of the two together, for instance allowing the melting point of the mixture to be finely tuned. It is also possible that the wax or wax-like material may be formed by the mixture of two or more different materials that may not themselves be individually wax like. It can be envisioned that a number of mixtures may be suitable for this purpose such as oils which have been thickened by the addition of metal soaps, clays and polymer additives designed to harden oils and fats such as silica gels, polypropylenes and polyethylenes. As will be appreciated by those skilled in the art, most naturally derived waxes are themselves typically complex mixtures of different chiefly hydrophobic chemical species. It should be appreciated that the foregoing list is not exhaustive but merely illustrative of the range of natural and synthetic waxes available to the formulator. For the purposes of this invention, a particular material may be chosen with the intention of providing a suitable barrier layer for the core particle and having the necessary chemical and physical characteristics such as solubility, melting temperature, barrier properties (i.e. a barrier to reactive species, water and other formulation ingredients), crystalline and/or amorphous properties and hardness which allow for application to the core particle and which provide for an effective barrier.

Amphiphilic Polymer

As mentioned above, in one preferred embodiment, the coating comprises a blend of at least one wax or wax-like substance and at least one amphiphilic polymer. Suitable amphiphilic polymers are described in WO 2009/068569, WO 2009/050203 and WO 2009/068570, all in the name of Revolymer.

The purpose of the amphiphilic polymer in admixture with the wax or wax-like material is to provide a locus of weakness when the mixture finds itself in a trigger environment i.e. when the external environment is such that the chemical functionality present in the amphiphilic polymer will respond to the environment and dissolve or disperse, thereby causing the destabilisation of the mixture itself which, when present as a coating, leads to the release of the core material.

The amphiphilic polymer therefore needs to be a material which may be mixed with the wax or wax-like material to produce either a single phase coating or a multiple phase coating or a solid dispersed within the wax or wax-like material and must contain chemical functionality which will respond to an external environment to produce a response in its chemistry.

In one preferred embodiment, the amphiphilic polymer is an amphiphilic copolymer.

As used herein, the term "copolymer" refers to a polymeric system in which two or more different monomers are polymerised together.

As used herein, the term "amphiphilic copolymer" refers to a copolymer in which there are clearly definable hydrophilic and hydrophobic portions.

In one preferred embodiment of the invention the polymer graft is a hydrophilic water soluble polymer that is able to act as the locus of weakness in the coating. For instance it may preferably be a poly(ethylene glycol)/poly(propylene oxide), poly(vinyl alcohol), poly(vinyl pyrrolidone), poly (styrene sulfonate), polyacrylamidomethylpropylsulfonic acid or similar molecules. Grafts like poly(ethylene/propylene glycol) are also preferred as they increase the ability of the system to react to changes in ionic strength.

The coating of the present invention may contain one or more amphiphilic copolymers. In one embodiment, the coating of the present invention comprises between about one and about four amphiphilic copolymers, for example one, two, three, or four copolymers, preferably one or two copolymers, most preferably one copolymer.

In one preferred embodiment of the present invention, the amphiphilic copolymer has a hydrophilic-lyphophilic (or hydrophobic) balance (HLB) as measured by Griffin's method of less than or equal to about 15, preferably less than or equal to about 10, more preferably between about 1 and about 10, yet more preferably between about 2 and about 9, for example, between about 3 and about 8. The Griffin method values are calculated by: hydrophilic-lyphophilic balance=20× molecular mass of the hydrophilic portion/molecular mass of the whole molecule.

The molecular mass of the hydrophilic and hydrophobic portions of the polymer can be estimated from the quantities of the relevant monomers put in as feedstocks in the manufacture of the amphiphilic copolymer and based on an understanding of the kinetics of the reaction. The composition of the final product can be checked by comparing the relevant intensities of signals from each block or portion using $^1$H nuclear magnetic resonance spectroscopy. Alternatively, other quantitative spectroscopic techniques such as infra-red spectroscopy or ultra-violet visible spectroscopy can be used to confirm the structure, provided the different portions give clearly identifiable and measurable contributions to the resulting spectra. Gel permeation chromatography (GPC) can be used to measure the molecular weight of the resulting materials As described herein there are available in the marketplace a range of amphiphilic copolymers which have been synthetically modified so as to produce a material which is responsive to a change in chemical environment or media. As used herein, "amphiphilic polymers" are those that have one or more well defined hydrophilic domains and one or more hydrophobic domains. Preferably, the amphiphilic polymer is a copolymer.

A wide range of amphiphilic copolymers may be suitable for use in the invention provided that they contain hydrophobic domains that are sufficient to ensure sufficient compatibility with the wax or wax-like material such that the encapsulates are stable in a formulated product. Any amphiphilic copolymer used in the invention must have sufficient hydrophilic functionality such that the amphiphilic polymer is responsive to changes in the formulation environment. As is well known in the art, in general the structures fall into several different forms of architecture including block copolymers, graft copolymers, highly branched and chain-extended or cross-linked polymers. A person skilled in the art of polymer chemistry would be familiar with such forms, together with methods for their preparation.

Many different polymers are suitable for use in the coating of the particle of the invention, provided they fulfil the key requirements of an amphiphilic polymer, that is to say they comprise a hydrophobic block that has compatibility with the wax or wax-like material, and a hydrophilic block capable of engineering responsiveness to changes in the environment.

By way of example, polymers comprising polyethylene glycol units, or portions (e.g. blocks or grafts) are particularly suitable for use as amphiphilic polymers in the context of the invention due to their responsive nature to ionic strength and to water activity. Preferably the hydrophilic portions may be based on a poly(alkylene oxide), such as polyethylene oxide or a copolymer thereof. Similarly preferred groups include polyglycidol, poly(vinyl alcohol), poly(ethylene imine), poly(styrene sulfonate) or poly (acrylic acid). Likewise polymers comprising poly(vinyl alcohol) units or portions are also responsive to changes in ionic strength and to water activity.

Particularly useful hydrophobic units or portions are those polymers based on hydrophobic monomers such as olefins (e.g. ethylene, propylene), dienes (e.g. butadiene or isoprene) and ethylenically unsaturated monomers such as isobutylene or octadecene. Aromatic monomers like styrene and alpha-methyl styrene may also be used. In a preferred embodiment, the hydrophobic portion may contain an acid, diacid or anhydride based monomer such as maleic anhydride. Acid and anhydride groups are preferred as they serve as a point of attachment and can potentially increase the responsiveness of the system.

A number of examples of suitable amphiphilic copolymers that have utility in the invention are given below.

Amphiphilic block copolymers may be manufactured by a variety of methods including the sequential addition polymerisation of two or more monomers in a linear manner typically using a living or controlled polymerisation technique. Alternatively they may be produced by the propagation and polymerisation of a polymeric chain from an existing polymer, or by chemically reacting well defined blocks together using coupling or click chemistry. A wide variety of such materials are available commercially and have utility in the invention Many commercial amphiphilic block copolymers materials are produced via the ethoxylation of a preformed alcohol functionalised hydrocarbon block. This hydrophobic block or domain may be, for instance, manufactured by the polymerisation of a hydrophobic monomer, chemical synthesis or processing of petrochemical or natural feedstocks e.g. by the isolation of natural fatty alcohols. The polymerisation of ethylene oxide is then initiated on the alcohol and propagates to form a polyethylene block.

In one highly preferred embodiment the amphiphilic polymer is a block copolymer of ethylene and ethylene oxide. In one highly preferred embodiment the amphiphilic polymer is selected from the range of block copolymers of ethylene and ethylene oxide known as Unithox™ (Baker Hughes) and may be a single product in this range or a mixture of two or more.

Unithox™ polymers are understood to be manufactured by the polymerisation of ethylene oxide (i.e. ethoxylation) from an alcohol functionalised polyethylene wax (which may also be described as a long chain saturated hydrocarbon alcohol). The ratio of PE to PEO in these materials has a profound effect upon their aqueous solution properties and in particular their HLB value (Hydrophilic/Lipophilic Balance) which is a calculation by which a particular amphiphilic material may be classified in terms of its hydrophilicity or hydrophobicity. Importantly, it is possible to identify certain ratios of PE:PEO within the Unithox™ range which, when coated as a layer onto a core particle will show good water-proofing properties when such particles are suspended into a low water containing media. 'Low water containing' refers to a liquid media which has approximately less than 20% water—as is often found in unit liquid dose and gel laundry products which may be packaged in dissolvable polymeric sachets. As mentioned above, such particles coated with Unithox™ are water-proof when exposed to a liquid media of low water content. However, the applicant has found that on dilution into water, such as in application usage when, for example, used in a laundry wash, the Unithox™ coating will dissolve/disperse and hence release the active core contents. The applicant has surprisingly found that Unithox™ behaves in a responsive manner to dilution/ionic strength. The applicant has also found that the blending of other hydrophobic materials, such as those described herein as the wax or wax-like material, into Unithox™ provides for a coating which has excellent stability, i.e. the active core when coated with a suitable blend of wax or wax-like material and Unithox™ is stable for extended periods in, for example, common commercial laundry products over significant periods of time and particularly products which have low water content (i.e. below around 20% water). Such particles coated, for example, with a suitable blend of water-proof material (e.g. wax or wax-like material) in combination with Unithox™ provides for excellent stability of the active core particles (the 'payload') but, due to the responsive nature of the Unithox™ will release the active upon application usage and will do so in a short enough timeframe to be suitable for use in typical household and industrial applications.

As mentioned above Unithox™ are block copolymers of commercially produced ethylene oxide with a hydrophobic (e.g. polyethylene) based block. It will be appreciated that it will be possible to form a similar structure by reacting a functionalised polyethylene material with an appropriately functionalised PEO (PEG) graft. For instance Baker Petrolite supply the Unicid™ range of materials which incorporate carboxylic acid functionality into a polyethylene based polymer wax and the CERAMER™ range—a polyethylene based polymeric material incorporating maleic anhydride functionality. These can potentially be reacted with mono alcohol or difunctional alcohol functionalised PEG resulting in the synthesis of AB or ABA amphiphilic block copolymers respectively.

Amphiphilic graft copolymers can be manufactured by several different methods, for instance a preformed backbone can be reacted with preformed grafts (sometimes called the "grafting to" method). Alternatively, polymerisation can be initiated from a suitably functionalised backbone such that the grafts are generated in situ ("grafting from" approach). Finally, a polymer or oligomer with a polymerisable group (a macromonomer) can be polymerised to yield a graft copolymer in which the original polymer chains are pendant to the backbone (the "grafting through" or macromonomer approach). Amphiphilic graft copolymers suitable for use in the invention typically contain suitable chemical functionality incorporated in the polymer backbone, or pendant to this, or grafted, or present in a random arrangement, or as blocks, or may be subjected to post-production functionalisation. In essence the material must include a hydrophile (X) and also a hydrophobe (Y) in the correct proportions so as to effect the required dissolution properties. Such constructs of X and Y shown in Scheme 1 below will be described in terms of various non limiting and common architectures available.

Scheme 1
Amphiphilic Graft Copolymer

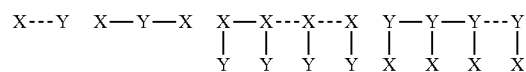

In one embodiment of the invention, the amphiphilic copolymer is a graft copolymer comprising a hydrophobic straight or branched chain carbon-carbon backbone having at least one hydrophilic side chain attached thereto.

In a preferred embodiment of the invention, the hydrophilic side chains of the graft copolymer are each independently of formula (I),

wherein $R^1$ and $R^2$ are each independently H, —C(O)WR$^4$ or —C(O)Q;

provided that at least one of $R^1$ and $R^2$ is the group —C(O)Q;

or $R^1$ and $R^2$ together form a cyclic structure together with the carbon atoms to which they are attached, of formula (II)

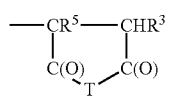

(II)

wherein:
$R^3$ and $R^5$ are each independently H or alkyl;
W is O or NR$^4$;
Q is a group of formula —X$^1$—Y—X$^2$P;
T is a group of formula —N—Y—X$^2$—P;
X$^1$ is O, S or NR$^4$;
X$^2$ is O, S, (CH$_2$)$_p$ or NR$^4$;
p is 0 to 6;
each R$^4$ is independently H or alkyl;
P is H or another backbone; and
Y is a hydrophilic polymeric group.

As used herein, the term "alkyl" encompasses a linear or branched alkyl group of about 1 to about 20 carbon atoms, preferably about 1 to about 10 carbon atoms, more preferably about 1 to about 5 carbon atoms. For example, a methyl group, an ethyl group, an isopropyl group, a n-propyl group, a butyl group, a tert-butyl group or a pentyl group.

In a preferred embodiment of the invention, the hydrophilic polymeric group Y is a poly(alkylene oxide), polyglycidol, poly(vinyl alcohol), poly(ethylene imine), poly(styrene sulfonate), polyacrylamidomethylpropylsulfonic acid or poly(acrylic acid). More preferably, the hydrophilic polymeric group Y is a poly(alkylene oxide), such as polyethylene oxide or a copolymer thereof.

In a further preferred embodiment of the invention, the hydrophilic polymeric group Y is of formula -(Alk$^1$-O)$_b$-(Alk$^2$-O)$_c$—, wherein Alk$^1$ and Alk$^2$ are each independently an alkylene group having from 2 to 4 carbon atoms, and b and c are each independently an integer from 1 to 125; provided that the sum b+c has a value in the range of from about 10 to about 250, more preferably, from about 10 to about 120.

In a further preferred embodiment of the invention, the graft copolymer has from 1 to 5,000, preferably from about 1 to about 300, and more preferably from about 1 to about 150, pendant hydrophilic groups attached thereto. For example, the graft copolymer may have between about 1 to about 10, between about 1 to about 5, or between about 2 to about 8 pendant hydrophilic groups attached thereto.

In an alternative embodiment of the invention, the amphiphilic copolymer is a graft copolymer comprising a hydrophilic straight or branched chain carbon-carbon backbone having at least one hydrophobic side chain attached thereto.

Where the amphiphilic copolymer is a graft copolymer, each side chain of the graft polymer preferably has a molecular weight from about 800 to about 10,000. For example, each side chain preferably has a molecular weight between about 1,000 to about 7,500, between about 2,500 to about 5,000 or between about 6,000 and about 9,000.

In another preferred embodiment of the invention, the amphiphilic copolymer is a block copolymer comprising hydrophilic blocks and hydrophobic blocks in a straight or branched chain carbon-carbon backbone.

In one preferred embodiment of the invention, the straight or branched chain carbon-carbon backbone has at least one side chain attached thereto. The side chain(s) may be hydrophobic or hydrophilic. Examples of suitable side chains include those described above with reference to amphiphilic graft copolymers. Preferably the block copolymer has a straight chain carbon-carbon backbone comprising hydrophilic blocks and hydrophobic blocks. In a further preferred embodiment, the amount of hydrophilic polymer by weight in the final composition is between from about 5 to about 60%.

A graft copolymer is typically produced by the reaction of hydrophilic grafts with a single reactive site on the carbon-carbon backbone, i.e. the reaction uses monofunctional grafts. In order to create a cross-linked or chain-extended copolymer it is necessary to incorporate a hydrophilic graft that has two sites that will react with the carbon-carbon backbone, i.e. a difunctional hydrophilic graft that can act as a cross-linking agent is used.

Preferably, the cross-linked or chain-extended copolymers comprise a linear or branched carbon-carbon backbone and a difunctional graft or a mixture of monofunctional and difunctional grafts. More preferably, the cross-linked or chain-extended copolymers comprise a carbon-carbon backbone functionalized with maleic anhydride or a derivative thereof (as described herein) and an alkylene oxide such as those described in formula (II). Most preferably, the cross-linked or chain-extended copolymers comprise a carbon-carbon backbone derived from polyisoprene or polybutadiene functionalized with maleic anhydride or a derivative thereof, and further comprise hydrophilic grafts, preferably being polyethylene oxide or a copolymer thereof.

In one preferred embodiment of the invention, the carbon-carbon polymer backbone is derived from a homopolymer of an ethylenically-unsaturated polymerizable hydrocarbon monomer or from a copolymer of two or more ethylenically-unsaturated polymerizable hydrocarbon monomers.

More preferably, the carbon-carbon polymer backbone is derived from an ethylenically-unsaturated polymerizable hydrocarbon monomer containing 4 or 5 carbon atoms.

In one highly preferred embodiment of the invention, the carbon-carbon polymer backbone is derived from isobutylene, 1,3-butadiene, isoprene or octadecene, or a mixture thereof.

In one preferred embodiment of the invention, the copolymer comprises a carbon-carbon backbone (e.g. polyisoprene or polybutadiene) onto which maleic anhydride or maleic anhydride acid/ester groups have been grafted. Preferably, the carbon-carbon backbone comprises from about 1 to about 50 wt % maleic anhydride group. As used herein, the term maleic anhydride (MA) group encompasses maleic anhydride, maleic acid and salts thereof and maleic acid ester and salts thereof and mixtures thereof.

The maleic anhydride group coupling chemistry provides a convenient method for attaching the grafts to the copolymer backbone. However, the skilled person would appreciate that other functional groups would be equally effective in this regard.

By way of example, the reaction of another acyl group (e.g. a suitable carboxylic acid or acyl chloride) with a hydroxyl functionalised polymer will be suitable for forming an ester linkage between the graft and backbone. Various strategies for performing coupling reactions, or click chemistry, are also known in the art and may be utilised by functionalising the backbone with suitable groups, possibly in the presence of a suitable catalyst. For instance the reaction of an alkyl or benzyl chloride group on the backbone with a hydroxyl group for instance (i.e. a Williamson coupling), or the reaction of a silicon hydride with an allyl group (a hydrosilyation reaction) could be utilised.

As used herein, the term "aryl" encompasses any functional group or substituent derived from an aromatic ring or a heteroaromatic ring, preferably a C6 to C20 aromatic ring, for example, phenyl, benzyl, tolyl or napthyl.

Preferably, the carbon-carbon backbone comprises from about 1 to about 50 wt % maleic anhydride.

In one preferred embodiment, the backbone of the amphiphilic polymer has a molecular weight from about 1,000 to about 10,000.

In another preferred embodiment of the invention, the carbon-carbon backbone is a copolymer of:
(i) maleic anhydride, maleic acid or salts thereof or maleic acid ester or salts thereof or a mixture thereof; and
(ii) one or more ethylenically-unsaturated polymerizable monomers.

The MA group monomer is thus present in the actual backbone rather than pendant to it.

A number of such materials are available commercially, most typically obtained by the radical polymerisation of a mixture of a maleic anhydride group and one or more other ethylenically unsaturated monomers. It will be envisioned that any number of monomers, though most typically a mixture of a maleic anhydride group and one other monomer (to make a bipolymer) or two other polymers (to make a terpolymer) will be used. Preferably, the maleic anhydride group monomer is maleic anhydride.

Preferably, the other monomer is ethylene, isobutylene, 1,3-butadiene, isoprene, a C10-C20 terminal alkene, such as octadecene, styrene, or a mixture thereof. Most preferably, the other monomer is isobutylene or octadecene.

The percentage of the monomers, and thus functionality in the resulting polymer, may be altered to provide optimal fit to the application. One advantage of backbones prepared by such a method is that they offer the potential for higher loadings of maleic anhydride potentially available for reaction with hydroxy, amine, or sufide functionalised grafts (e.g. suitable PEOs, MPEOs or amine functionalised alkyl ethxoylates like certain Jeffamines).

In one aspect of the invention the backbone is an alternating copolymer prepared by mixing and subsequently polymerising equimolar quantities of a MA group and another monomer.

A particularly preferred backbone copolymer is poly(isobutylene-alt-maleic anhydride) (PIB-alt-MA):

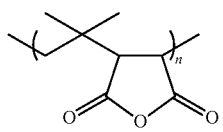

wherein n is between 5 and 4000, more preferably 10 and 1200.

This polymer is available commercially from Sigma-Aldrich and Kuraray Co. Ltd; Kuraray supply the material under the trade name ISOBAM.

A further preferred backbone copolymer is poly(maleic anhydride-alt-1-octadecene) (C18-alt-MA) (available from the Chevron Philips Chemical Company LLC).

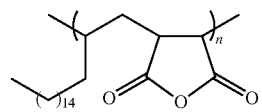

wherein n is between 5 and 500, more preferably 10 and 150.

Chevron Philips make a range of materials (both high and low viscosity) in their PA18 Polyanhydride resins range that are preferred backbones in the invention. PA18 is a solid linear polyanhydride resin derived from 1-octadecene and maleic anhydride in a 1:1 molar ratio.

It will be appreciated by those skilled in the art that a number of other backbones in which maleic anhydride is included in the backbone, either by grafting the maleic anhydride as an adduct, or by copolymerising maleic anhydride with one or more other monomers are useful in the invention.

A range of polybutadiene polymers functionalised with maleic anhydride are sold under the Ricon brand by Sartomer (e.g. Ricon 130MA8) and Lithene by Synthomer (e.g. N4-5000-5MA). A particularly preferred backbone is Lithene N4-5000-5MA. A further particularly preferred backbone is Lithene N4-5000-15MA. A number of useful backbones are also manufactured by Kraton (e.g. Kraton FG) and Lyondell (e.g Plexar 1000 series) in which maleic anhydride is grafted onto polymers or copolymers of monomers such as ethylene, propylene, butylene, styrene and/or vinyl acetate.

Poly(styrene-alt-maleic anhydride) is available from a number of suppliers including Sartomer under the SMA trade name. Poly(ethylene-alt-maleic anhydride) is available from a number of suppliers including Vertellus under the ZeMac trade name. Poly(methyl vinyl ether-alt-maleic anhydride) is available from International Speciality Products under the Gantrez trade name. Poly(ethylene-co-butyl acrylate-co-maleic anhydride) materials can be obtained from Arkema, and are sold under the trade name of Lotader (e.g. 2210, 3210, 4210, and 3410 grades). Copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) are also available and also sold in the Lotader range. A number of the Orevac materials (grades 9309, 9314, 9307 Y, 9318, 9304, 9305) are suitable ethylene-vinyl acetate-maleic anhydride terpolymers.

In many cases in addition to, or instead of a maleic anhydride functionalised material a derivative of a diacid, mono ester form, or salt is offered. As will be obvious to those skilled in the art many of these are also suitable in the invention.

Similarly, suitable side chains precursors are those discussed below, such as mono methoxy poly(ethylene oxide) (MPEO), poly(vinyl alcohol) and poly(acrylic acid). These may for instance be purchased from the Sigma-Aldrich company. Suitable polyethylene imines are available from BASF under the Lupasol trade name.

In one preferred embodiment, the amphiphilic copolymer is prepared by reacting a compound of formula (III),

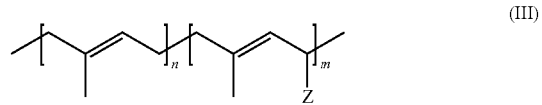

(III)

wherein Z is a group of the formula (IV),

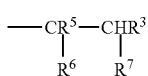
(IV)

wherein $R^3$ and $R^5$ are each independently H or alkyl, and $R^6$ and $R^7$ are each independently H or an acyl group, provided that at least one of $R^6$ and $R^7$ is an acyl group, or $R^6$ and $R^7$ are linked to form, together with the carbon atoms to which they are attached, a group of formula (V),

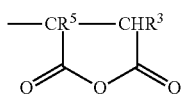
(V)

where n and m are each independently an integer from 1 to 20 000. Preferably m is 1 to 1000, more preferably 1 to 100 and yet more preferably 10 to 50. Preferably n is 1 to 5000, more preferably 5 to 2000 and yet more preferably 10 to 1000. Preferably, m is 1 to 100 and n is 5 to 2000.
with a side chain precursor of formula (VI)

$$HX^1\text{—}Y\text{—}X^2P \qquad (VI)$$

wherein:
$X^1$ is O, S or $NR^4$;
$X^2$ is O, S, $(CH_2)_p$ or $NR^4$;
p is 0 to 6;
each $R^4$ is independently H or alkyl;
P is H or another backbone; and
Y is a hydrophilic polymeric group.

In one preferred embodiment, the amphiphilic copolymer is prepared by reacting a compound of formula (IIIa),

(IIIa)

where n and m are as defined above, with a side chain precursor of formula (VI) as defined above.

In one preferred embodiment, the side chain precursor is of formula (VIa)

(VIa)

wherein $X^1$ is O or NH and $X^2$ is $(CH_2)_p$ and o is an integer from 5 to 250, preferably 10 to 100.

In another preferred embodiment, the side chain precursor is of formula (VIb)

(VIb)

wherein R is H or alkyl, $X^1$ is O or NH and $X^2$ is $(CH_2)_p$ and the sum of a and b is an integer from 5 to 600, preferably 10 to 100.

In one particularly preferred embodiment of the invention, the copolymer is prepared by grafting a monofunctional hydrophilic polymer such as poly(ethylene glycol)/poly(ethylene oxide) onto the maleic anhydride residues on the carbon-carbon backbone to form an amphiphilic copolymer of formula (VII),

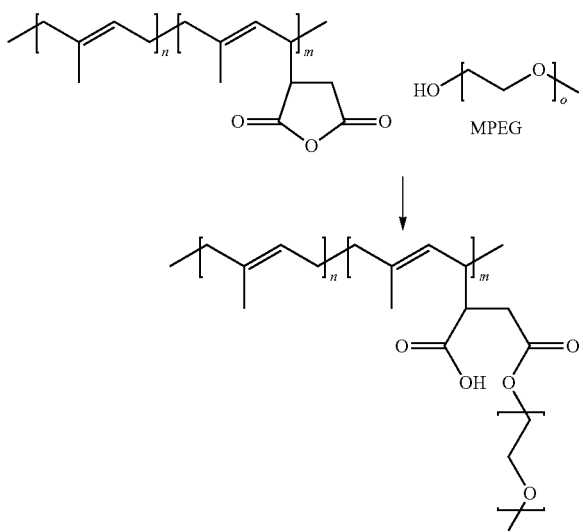
(VII)

wherein each of m and n is independently an integer from 1 to 20,000. Preferably m is 1 to 1,000, more preferably 1 to 100 and yet more preferably 10 to 50. Preferably n is 1 to 5,000, more preferably 5 to 2,000 and yet more preferably 10 to 1,000. Preferably, m is 1 to 100 and n is 5 to 2,000. Preferably o is an integer from 5 to 600, preferably 10 to 100.

The above example shows an alcohol functionalized PEO reacting with the maleic anhydride on a PIP-g-MA backbone. Suitable PIP-g-MA backbones are commercially available (for example, LIR-403 grade from Kuraray, which has approximately 3.5 MA units per chain).

Further details on functionalizing polyisoprene with maleic anhydride may be found in WO 06/016179, WO 08/104546, WO 08/104547, WO 09/68569 and WO 09/68570, the contents of which are herein incorporated by reference.

In one preferred embodiment, the copolymer is prepared by adding a ratio of 2:8 equivalents of MPEG with respect to each maleic anhydride (MA) group. This essentially enables complete conversion of the maleic anhydride groups into the PEG functionalized esters.

In another preferred embodiment, the copolymer is prepared by adding a 1:1 ratio of methoxy poly(ethylene oxide) (MPEO) to maleic anhydride. After complete reaction of the MPEO, another (second) (dihydroxy) poly(ethylene oxide) (PEO) of any molecular weight (e.g. 2,000, 4,000, 6,000, 8,000 and 10,000) can be added. It will be understood by those skilled in the art that MPEO, poly(ethylene oxide) methyl ether, methoxy poly(ethylene glycol) (MPEG), and poly(ethylene glycol) methyl ether are alternative methods of naming the same structure. Similarly PEO is also sometimes referred to as poly(ethylene glycol) (PEG) in the art.

In addition to functionalising unreacted maleic anhydride units, it is also possible to graft PEG or another graft onto the corresponding diacid or a mono ester derivative of MA.

This will result in new PEG ester links in the place of the COOH functionality. Two suitable backbones are illustrated below.

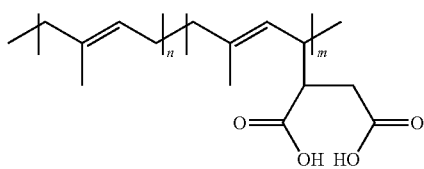

Diacid

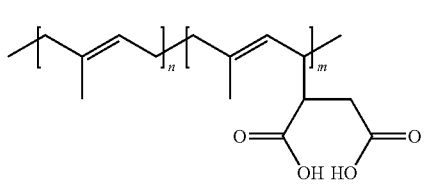

Polyisoprene-graft-
maleic acid/monomethylester
(PIP-g-MAMME)

Thus, in one particularly preferred embodiment, the amphiphilic copolymer is prepared by reacting a polymer precursor of formula (IIIb), (IIIb)

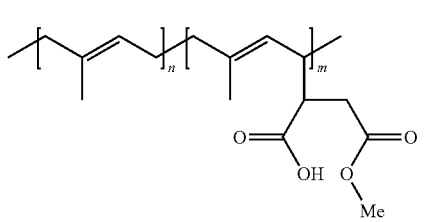

where n and m are as defined above, with a side chain precursor of formula (VI) as defined above.

In another particularly preferred embodiment, the amphiphilic copolymer is prepared by reacting a polymer precursor of formula (IIIc), (IIIc)

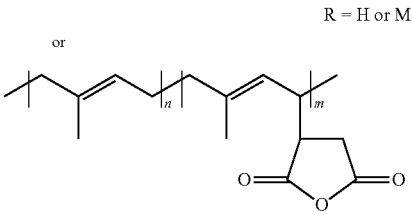

where n and m are as defined above, with a side chain precursor of formula (VI) as defined above.

In an alternative preferred embodiment, the copolymer is derived from —SH or nitrogen based ($NH_2$ or NHR) moieties.

In one particularly preferred embodiment, the copolymer comprises an $NH_2$ functionalized material. Preferably, for this embodiment, the amphiphilic copolymer is prepared from a side chain precursor of formula (VIc)

(VIc)

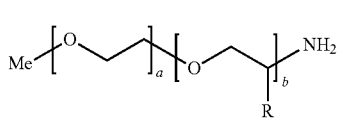

wherein R is H or alkyl, more preferably H or Me, and the sum of a and b is an integer from 5 to 250, preferably 10 to 100.

More preferably, the amphiphilic copolymer is of formulae (VIIIa) or (VIIIb) and is prepared by the following reaction:

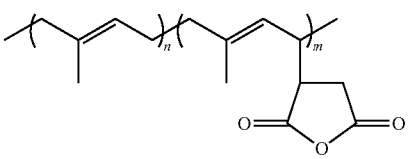

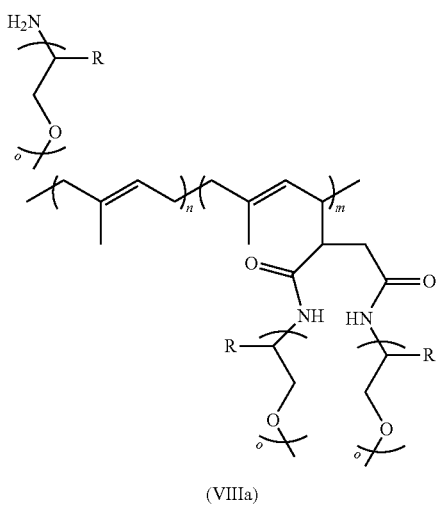

(VIIIa)

R = H or Me or

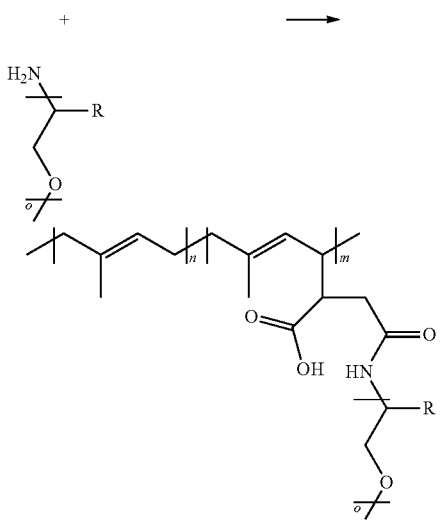

(VIIIb)

R = H or Me wherein each of m and n is independently an integer from 1 to 20,000. Preferably m is 1 to 1,000, more preferably 1 to 100 and yet more preferably 10 to 50. Preferably n is 1 to 5,000, more preferably 5 to 2,000 and yet more preferably 10 to 1,000. Preferably, m is 1 to 100 and n is 5 to 2,000. Preferably o is an integer from 5 to 600, preferably 10 to 100.

The NH₂ functionalized material depicted above comprises two grafts on each MA, which is not possible with MPEO. This is due to the greater reactivity of the NH₂ groups compared with OH. In addition to grafting two chains per maleic anhydride unit, the greater reactivity of the NH₂ units with respect to OH leads to a product containing very small quantities of free graft.

In one particularly preferred embodiment of the invention, the amphiphilic copolymer comprises a polybutadiene backbone and pendant hydrophilic grafts attached thereto, wherein each hydrophilic graft is derived from an NH₂ functionalised ethylene oxide and propylene oxide copolymer.

In any of the above embodiments, the compounds of formula (III) may be replaced by compounds of formulae (IX) and (X):

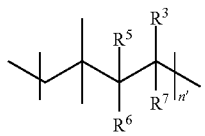
(IX)

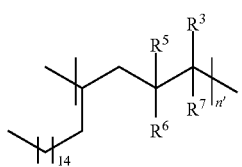
(X)

wherein n' is 5 to 4,000 and $R^3$, $R^5$, $R^6$ and $R^7$ are as previously defined.

Similarly, compounds of formulae (IIIa), (IIIb) and (IIIc) in any of the embodiments above may be replaced by compounds of formulae (IXa) or (Xa); (IXb) or (Xb); and (IXc) or (Xc), respectively:

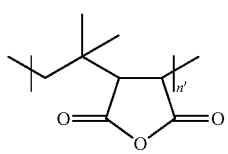
(IXa)

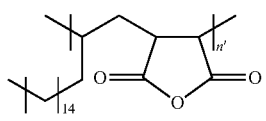
(Xa)

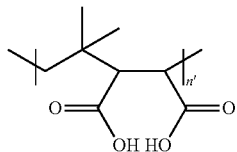
(IXb)

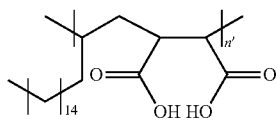
(Xb)

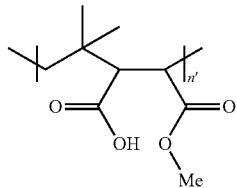
(IXc)

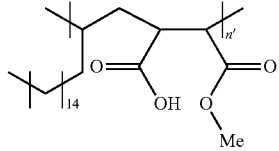
(Xc)

wherein n' is as defined for compounds of formulae (IX) and (X).

In one preferred embodiment, the hydrophilic groups grafted onto the maleic anhydride groups are polymers of ethylene oxide (i.e. PEOs) copolymerised with propylene oxide. In this embodiment, the amount of propylene oxide is preferably between 1 and 95 mol percent of the copolymer, more preferably between 2 to 50 mol percent of the copolymer, and most preferably between 5 to 30 mol percent of the copolymer.

Preferably, the side chain precursor is of formula,

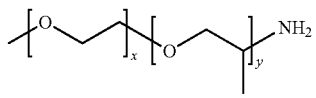

wherein x is 5 to 500, more preferably 10 to 100 and y is independently 1 to 125, more preferably 3 to 30. Preferably, x+y=6 to 600, more preferably 13 to 130. The distribution of ethylene and propylene oxide units may be in the form of blocks as depicted above or as a statistical mixture. In any case the molar ratio of ethylene oxide to propylene oxide in the copolymer will favour ethylene oxide. Such side chain precursors are sold commercially by Huntsman under the Jeffamine brand and Clariant under the Genamin name.

A particularly preferred embodiment is the graft copolymer formed from the reaction of Lithene N4-5000-5MA with the Jeffamine known as M2070. Also a particularly preferred embodiment is the graft copolymer formed from the reaction of Lithene N4-5000-15MA with the Jeffamine known as M2070.

Alternatively, it is possible to use a polymer that has two rather than one functional (e.g. OH, NH₂) units, in which both groups can react with the maleic anhydride. If these maleic anhydride groups are on different backbones, a cross-linked (or network) polymer can be formed. By controlling the ratio of graft to backbone, or by using mixtures with mono-functionalised materials, the degree of cross-linking can be controlled. Thus, it is possible to produce a material that resembles a chain extended graft copolymer (i.e. 2 or 3 graft copolymers) rather than a network by using a mixture of PEO and MPEO which chiefly comprises MPEO.

In one preferred embodiment, the amphiphilic copolymer is prepared from a mixture of PIP-g-MA (polyisoprene with grafted maleic anhydride) together with MPEO (methoxy poly(ethylene oxide) and/or PEO poly(ethylene oxide). Preferably, the MPEO and PEO have a molecular weight of about 2,000.

In one preferred embodiment, the amphiphilic copolymer is prepared from a mixture of PIP-g-MaMme (polyisoprene with grafted maleic monoacid monoester) together with MPEO (methoxy poly(ethylene oxide)) and/or PEO (poly (ethylene oxide)). Preferably, the MPEO and PEO have a molecular weight of about 2,000.

Example methodologies for the manufacture of the graft copolymers may be found in PCT/EP2008/066257 (WO 09/068570), PCT/EP2008/063879 (WO 09/050203) and PCT/EP2008/066256 (WO 09/068569), the teachings of which are incorporated herein by reference.

In an alternative embodiment of the invention, the amphiphilic copolymer is a cross-linked/network (or chain-extended) copolymer. Copolymers of this type may be prepared using the same or similar carbon-carbon polymer backbones to those described above in respect of amphiphilic graft copolymers. In one embodiment of the invention, the amphiphilic copolymer is a cross-linked/network copolymer comprising a hydrophobic straight or branched chain carbon-carbon backbone having at least one hydrophilic side chain attached thereto.

Coating Process

Coating of the particles may be carried out by any suitable means and the method is not critical to the invention. For example, the coating material may be sprayed on as a molten material or as a solution or dispersion in a solvent/carrier liquid which is subsequently removed by evaporation. The coating material can also be applied as a powder coating e.g. by electrostatic techniques, although this is less preferred as the adherence of powdered coating material is more difficult to achieve and can be more expensive. If layer coatings are applied in particle form (such as powders or dispersions), it may also be necessary to coalesce the particles which make up each layer in order to produce a layer which is sufficiently coherent, without appreciable levels of flaws such as cracks, holes or 'flakiness', to produce a sufficiently effective barrier.

Molten coating is a preferred technique for coating materials of melting point <80° C. but is less convenient for higher melting points (i. e. >100° C.). For coating materials of melting point >80° C., spraying on as a solution or dispersion is preferred. Organic solvents such as ethyl and isopropyl alcohol or chloroform can be used to form the solutions or dispersions depending on the nature and solubility of the solute, although this will necessitate a solvent recovery stage in order to make their use economic.

Application, in the case of waxes and/or other hydrophobic materials, from the molten state is particularly advantageous as this method allows for the potential for the direct application of up to 100% solids and avoids complications such as solvent recovery, allowing time for drying and the issues associated with the safe handling of volatile and potentially flammable solvents.

Application from solvent solution(s) is advantageous as the coating materials may be applied as a continuous and homogenous film from solvent solution. Any suitable solvent may be used accepting that consideration for volatility, boiling point, solubility of materials within the solvent, safety and commercial aspects is undertaken.

Solutions are particularly advantageous, where possible, provided the solution has a sufficiently low viscosity to enable it to be handled. Preferably a concentration of from about 5% to about 50% and preferably from about 10% to about 25% by weight of the coating material in the solvent is used in order to reduce the drying/evaporation load after surface treatment has taken place. The treatment apparatus can be any of those normally used for this purpose, such as inclined rotary pans, rotary drums and fluidised beds.

In one highly preferred embodiment, the coating is applied to the particle cores either by fluid bed coating or fluid bed drying. The coating material is applied to the core units from either the molten state or from solvent solution. Suitable plasticisers may also be employed to produce continuous films. The polymer is preferably applied to the particle core units as either a solution from solvent or from an emulsion or latex. In one embodiment, where the polymer is applied as an alkaline coating solution such as for the application of a pH responsive polymer, preferably the solution further comprises a stabilizer, for example, ammonia. Aqueous alkaline solutions of the polymer are prepared by neutralisation of the acidic latex. Neutralisation with volatile amines, such as ammonia, trimethyl amine, triethyl amine, ethanolamine and dimethylethanolamine, are preferred as the volatile component is readily lost and a robust polymer coating is readily achieved. Typically neutralisation is accompanied by clarification of the coating mixture, from an opaque latex to a clear or hazy solution, and an increase in viscosity. Additional solvent may be added to reduce the polymer concentration and solution viscosity and so obtain a solution suitable for further processing.

In one highly preferred embodiment, the coating is applied from a dispersion of a wax or wax-like substance and an amphiphilic polymer and other optional ingredients including surfactants, plasticisers, cosolvents, fillers etc.

There are a number of different methods known in the art for making dispersions from waxes/polymers which may be utilised for the manufacture of aqueous dispersions used in this invention. In order for a dispersion to be stable it is necessary to control the particle size of the dispersed hydrophobic phase (e.g. the wax or wax like substance and/or amphiphilic polymer phase) in order to ensure that the dispersed phase does not settle out of suspension. To achieve this it is typically necessary to carefully control the method of addition of the hydrophobic material or blend (i.e. non-aqueous phase) to the water (or visa-versa) in the presence of chemical dispersants and/or surfactants whilst applying sufficient agitation/mechanical sheer to break up the oil phase. This hydrophobic phase may comprise the wax or wax like substance in the molten state and may also comprise a molten solution in combination with the amphiphilic polymer (e.g. the dispersion is hot and so the dispersed phase exists within the dispersion as liquid droplets). This hydrophobic phase may alternatively comprise the wax or wax like substance in the solid state and may also comprise a solid solution in combination with the amphiphilic polymer (e.g. the dispersion is cold, below the solidification point of the hydrophobic dispersed material and so will be a dispersion of solid particles). The amphiphilic polymer may be self dispersing meaning it is able to facilitate its emulsification and stabilisation in the water phase. Alternatively, if the polymer is not readily dispersible then surfactants may be required to disperse the polymer; these may be mixed into the oil phase prior to dispersion or may be present in the water phase prior to dispersion. It may also be necessary to include a plasticiser within the dispersion formulation so as to improve the coherency of the film which is produced from the coated emulsion. Typically materials which are solvents for the hydrophobic phase, such as chlorinated solvents, terpenes, hydrogenated rosin derivatives, hydrocarbon solvents or other substances which have at least a small solubility in the hydrophobic phase, are suitable. It should be recognised that, in the case of the amphiphilic substance, it may be present in both phases of the dispersion as it will have compatibility in both the hydrophobic and hydrophilic portions of the dispersion.

Generally, methods for creating dispersions may be divided into two processes. In the first of these, often referred to as the 'direct method', the hydrophobic phase is added in a controlled manner to the stirred aqueous phase resulting in the formation of dispersed particles in the water. An alternative method for manufacturing the dispersion is the inversion method, in which the aqueous phase is added to the hydrophobic phase. Initially the product of this process is the forced formation of an emulsion of water in the hydrophobic phase, however upon continued addition of the aqueous phase the system inverts to a dispersion of the hydrophobic phase in water.

Surfactants may be used in the manufacture of a dispersion to stabilise the colloidal dispersion of hydrophobic phase in water. In a preferred embodiment, one or more surfactants are added to either the aqueous or hydrophobic phase or both. In the case of the aqueous phase, the surfactant is typically dissolved in water prior to use. When added to the hydrophobic phase, the surfactant may be dissolved in any solvent present or may, for instance, be dissolved or dispersed into the molten wax or wax like substance.

A wide range of surfactants may be used, including non-ionic, anionic or cationic or zwitteronic (amphoteric) structures. The identity and chemistry of the surfactant used to stabilise the system is preferably selected to avoid incompatibility with the final formulation media.

In one highly preferred embodiment of the invention, cationic surfactants are used. These help to stabilise the formation of a stable dispersion, but once the core particles have been coated with the dispersion and the coated particles are then suspended in, for example, a laundry product containing anionic surfactant, the interaction between the cationic surfactants in the coating and the anionic surfactants in the media leads to the formation of an extra layer of this neutralised material and an increase in the barrier properties of the coating.

Conversely, in an alternative preferred embodiment of the invention, anionic surfactants are used. These help to stabilise the formation of a stable dispersion, but once the core particles have been coated with the dispersion and the coated particles are then suspended in, for example, a laundry product containing cationic surfactant the interaction between the anionic surfactants in the coating and the cationic surfactants in the media leads to the formation of an extra layer of this neutralised material and an increase in the barrier properties of the coating.

Other water soluble materials which behave as emulsifiers, such as polyvinyl alcohol or other water soluble polymers and non-ionic surfactants, may be used so as to produce a stable dispersion having small dispersed droplet size. Polymeric surfactants may also be used.

The addition of surfactants and/or emulsifiers to stabilise the dispersion may result in the entrapment of air and subsequent foaming which can interfere with efficient manufacture of the dispersion. Thus, in one particularly preferred embodiment, an anti foaming agent is added to the aqueous and/or hydrophobic phase prior to dispersion manufacture in order to suppress the generation of foam.

In fluid bed coating the particulate core particles are fluidised in a flow of hot air and the coating solution, melt, emulsion or latex sprayed onto the particles and dried, where the coating solution. Melt, emulsion or latex may be applied by top spray coating, bottom spray (Wurster) coating or tangential spray coating, where bottom spray (Wurster) coating is particularly effective in achieving a complete encapsulation of the core. In general, a small spray droplet size and a low viscosity spray medium promote uniform distribution of the coating over the particles.

In fluid bed drying the particulate core particles are mixed with the coating solution, emulsion or latex and the resulting moist product introduced to the fluid bed dryer, where it is held in suspension in a flow of drying air, where it is dried or in the case of molten material is congealed. Such systems are available from several suppliers including GEA Process Engineering (Bochum, Germany) and Glatt Process Technology (Binzen, Germany).

It will be appreciated that any method which allows for the application of an essentially continuous film of material may be used to produce the layers described herein and that the processes described are illustrative and not exhaustive of methods, such as curtain coating, other forms of spray coating and any other suitable methods which is able to produce substantially the same particle layer structures described herein.

The present invention is further described by way of the following non-limiting examples.

Examples

The present invention is clarified by means of the following exemplary embodiments:
SP refers to a spheronised particle;
CE refers to a comparative example (uncoated), prepared from Example 1 in WO 2012/066344;
CN refers to a chopped noddle format.

The process of preparing and coating the bleach-containing particles was performed via the following processes:
1. Preparation of a wet-mass;
2. Extrusion of the wet mass;
3. Shaping of the wet mass such as by chopping or spheronisation of the wet mass;
4. Drying and optionally coating of the wet mass.

Components, Abbreviations and Sources of Materials
Eureco WM1 or Eureco MG—6-phthalimidoperoxyhexanoic acid (PAP)—Solvay
Cross-linked polyacrylic acid (Produkt Z1069)—Evonik
Cross-linked polyacrylic acid (Produkt T5066F)—Evonik
Kolloidon CL-M or CL-F—BASF
Luvicross—BASF
Lycotab C, PGS or SSH—Roquette Corporation
Maize Starch—Aldrich Chemical Co
Potato Starch—Aldrich Chemical Co
Potato Starch (Industrial Grade)—Roquette Corporation
Rice Starch—Aldrich Chemical Co
Wheat Starch—Aldrich Chemical Co
Ascorbic acid—Aldrich Chemical Co
Bentonites—Ca form, $Na_2CO_3$ or Na Citrate form—Amcol Minerals Europe Ltd
Buteraldehyde—Aldrich Chemical Co
Carbopol 971 PNF—Lubrizol Corporation
Carbopol 980—Lubrizol Corporation
Carbopol Aqua SF1—Lubrizol Corporation
Carbopol Aqua SF2—Lubrizol Corporation
Dequest™ 2060—Akzo Nobel N.V.
Dissolvine™ GL-47-S—Akzo Nobel N.V.
2-Dodecene-1-yl-Succinic Anhydride—Aldrich Chemical Co
EDTA—Aldrich Chemical Co
Etidronic acid—1-hydroxy-ethylene-1,1-diphosphoric acid (HEDP)—Aldrich Chemical Co
Emcosoy—JRS Pharma 5-Gluconolactone—Aldrich Chemical Co
Hostapur SAS (93)—Clariant
Isomalt (Galen IQ Sourced)—Beneo Orafti Gmbh
Jeffamine M2070—Huntsman
Lactic Acid—Aldrich Chemical Co
Lithene N4-5000-5MA—Synthomer
Malic Acid—Aldrich Chemical Co
Malonic Acid—Aldrich Chemical Co
Microcrystalline Cellulose (Avicel PH)—Aldrich Chemical Co
Molwiol®—Kuraray Chemical Co
Noveon AA-1-Lubrizol Corporation
Oxalic acid—Aldrich Chemical Co
Pectin (pectinic acid))—Aldrich Chemical Co
Phosphoric acid—Aldrich Chemical Co
Poly(itaconic acid)—Revolymer Ltd
Sorbitol—Roquette Corporation
Talc—Aldrich Chemical Co
Vybar 260—Baker Hughes Formation of the wet mass was performed on a food grade Kenwood FPP220 Multipro Compact mixer the extrusion was perfumed on a Caleva Variable Density Extruder with the 0.7 mm diameter hole die plate. The spheronisation was performed on a Caleva Multi Bowl Spheroniser 250 (MBS250). Drying of the particles was performed on a Aeromatic Fielder Strea 1 and coating of the dried particles was conducted on Glatt Mini Glatt 5 for small scale coating and on the Strea for larger samples.

Example SP1—Preparation of a Spheronised PAP-Core

Preparation of the Binder Fluid

Hostapur® SAS 93 (100 g) was added to deionised water (200 g) and stirred with heating to 60° C. until the Hostapur® had dissolved. The sample was then cooled to room temperature.

Preparation of the Wet Mass

Eureco WM1 (150.22 g) (previously sieved to less than 250 μm) was weighed into the bowl of a Kenwood mixer to this was added Lycotab PGS (6.33 g), cross-linked poly (acrylic acid) (Produkt Z1069) (6.33 g) and anhydrous citric acid (5.03 g). The mixer lid was then secured with the chute lid inserted into the addition tube and the powder mixture was blended at speed "2" for 5-10 seconds to ensure a homogenous powder mixture. Following this, etidronic acid (60% solution) (2.23 g) was added from a pipette drop-wise whilst mixing the powders. The previously prepared binder fluid (approx 50 mL) was then added at a constant rate over 5-10 seconds whilst mixing. The binder fluid was added until a change in pitch of the mixing sound occurred, at this point the dough formed a breadcrumb-like appearance, and the total binder addition was recorded. The sides of the bowl were then scraped with a plastic spatula and the lid replaced on the mixer, the sample was then mixed for a further 10 seconds.

Extrusion of the Wet Mass

The prepared wet-dough was then added to the extruder and extruded at room temperature using a screw speed of 50 rpm. The extruded noodles were then either divided with a spatula to obtain chopped "noodles", as in the case of examples CN1 and CN2, of 0.5-3 cm in length or retained for subsequent spheronisation.

Spheronisation of the Extrudate

Spheronisation took place at a plate rotation speed of 950 rpm. The prepared extrudate was added in batches of around 220 g to the spheroniser for around 1 to 3 minutes or until the particles generated were of an acceptable spherical form.

Preparation of Chopped Noodles

The extruded mass was manually chopped with a spatula to a length of approximately 5 mm and the resultant materials were dried overnight in a vacuum oven at 30° C. and used in the stability testing.

Drying of the Product

The resultant spheronised particles were dried in the fluid bed drier at 35° C. for up to 2 hours at an air flow rate which ensured good fluidisation of the sample, typically between 50 to 120 m$^3$/hr, to ensure the majority of the moisture was removed from the particles. If necessary, an additional drying step was performed where the product was dried in a vacuum oven at 35° C. for 18 hours.

Coating of the Materials

A particularly useful class of materials which can be used to coat the pre-formed PAP-containing particles are functionalised or un-functionalised poly(vinyl alcohols-co-vinyl acetate) such as those provided by the Kuraray Co Ltd such as the Mowiol® series of materials. These materials have the general nomenclature Mowiol® X-Y where the value for X represent the viscosity (in mPas) of a 4% w/w aqueous solution of the polymer and Y represents the molar % hydrolysis of the starting poly(vinyl acetate).

In the case of sample CP1, an emulsion coating was used based on a wax with a pre-formed amphiphilic graft copolymer. This coating was prepared as follows:

Reaction of Polybutadiene-Graft-Maleic Anhydride Lithene N4-5000-5MA Grade with Jeffamine M2070 (Preparation of AGC1) in a Reaction Flask PBD-g-MA (200 g, Polybutadiene-graft-maleic anhydride obtained from Synthomer, Lithene N4-5000-5MA grade) having an average molecular weight of approximately 5,750 Da was weighed out and added to a reaction flask with a 0.5 L capacity, equipped with an overhead stirrer. A flow of nitrogen gas was passed through the vessel, which was then heated to 150° C. using an oil bath. Stirring of the molten mixture then commenced and Jeffamine M2070 (Polyether monoamine) (144 g, purchased from Huntsman), having an average molecular weight of 2,000 Da was added over 45 minutes via a dropping funnel. The reaction mixture was maintained at 150° C. for a total of approximately 6 hours with stirring. Following this it was allowed to cool and was then dispensed into a glass container.

An emulsion of Vybar 260 and AGC1 was produced using the following method. AGC1 (1.5 g) was dissolved in deionised water (190 g) with stirring. This solution was heated to 65° C. and mixed with a Silverson L4R mixer at speed 1, a melt of Vybar 260 (8.5 g) was added to the solution drop-wise over the course of 2 minutes and the speed increased to speed "2" for a further 2 minutes. The warm mixture was then sonicated with a sonic probe for up to 10 minutes, creating an emulsion. The emulsion was cooled immediately on an ice/water bath swirling the emulsion occasionally. The emulsion was stirred throughout the spray coating process (coating process as described above for solvent based solutions).

Functionalisation of the Polymers

The following procedure was used to functionalise the Mowiol® polymers with buteraldehyde altering the type and feed ratios of Mowiol® and buteraldehyde where necessary. All other processes and timings remained constant.

Preparation of a 100 g Batch of Mowiol® 10-98+8% Butyraldehyde

A 2-litre flanged flask was charged with Mowiol® 10-98 (100 g) and deionised water (900 g). The flask was placed onto a heating block and fitted with a head unit, anchor stirrer, nitrogen line, condenser and bubbler. The mixture was then heated to 80° C. and stirred under nitrogen for 1 hour or until all Mowiol® had dissolved. After this time, the temperature of the heating block was reduced to 60° C. and 2M HCl (13.4 mL, 27 mmol) was added followed by butyraldehyde (6.42 g, 89 mmol). The reaction was stirred with heating at 60° C. under an atmosphere of nitrogen for a further 4 hours. After this time the heating block was turned off and the mixture was stirred overnight under an atmosphere of nitrogen at room temperature. After this time, the reaction mixture was neutralised to pH 7 using dilute ammonia solution and the reaction product was precipitated by drop-wise addition of the reaction mixture to an stirred excess of acetone at room temperature (4 litres total). The precipitate was then filtered off and dried in a vacuum oven at 40° C. overnight. Where the coating of the polymers stipulates un-neutralised, the neutralisation step using ammonia solution was omitted.

Coating of the Preformed Particles

Two fluidised bed driers were used for this purpose: a Glatt Mini Glatt 5 and an Aeromatic Fielder Strea 1. Both systems were equipped with a Gilson Miniplus 2 peristaltic pump. The cores to be coated were weighed directly into the coating container, 50 g for Mini Glatt process, up to 1 kg for Strea. The airflow and atomising pressure was adjusted so that the particles flowed, typically between 0.3-0.7 bar and 0.3-0.5 bar respectively. Once a stable bed was achieved the polymer solution (5% w/w) was added at a rate of approx 0.3 to 1 g/min for the Mini-Glatt and 0.6 to 3 g/min for the Strea drier. The rate of polymer addition was increased during the coating process after the initial 30 minutes, essentially once a stable fluidised bed was achieved. The temperature of the fluidised bed was set to a suitable level for the coating to dry and the core to be stable, typically around 30 to 35° C. (the inlet temperature is around 5 to 10° C. higher). The coating process was completed after ~30 to 900 minutes depending upon the scale and flow rate of the polymer addition. Following the coating the coated particles were removed from the driers and stored for further testing.

The polymer solutions or emulsions were coated onto pre-prepared pre-dried PAP core samples of equivalent compositions to those prepared previously, for example samples SP 53a to SP53g were based on the original SP53 composition and the formation of these materials were repeated each time to produce the base materials to coat. In each case the assay and elevated stability of the pre-coated cores was determined by the standard iodometric titration and incubation at 40° C. The results for selected particles according to the invention are set forth in Tables 1-7.

Screening of the Materials

The prepared PAP materials were screened for their stability in isolation at elevated temperatures and in detergent powder formulations. The activity of the PAP in the core materials was determined before, in order to obtain the assay value, and after incubation via the procedure described below.

For the elevated temperature incubation procedure the PAP samples, 0.2 g, were added to a 5 mL plastic tube and sealed. The tubes were then placed in an incubator at 40° C. for 7 and 35 days and then analysed in triplicate for the PAP levels as described below.

For the in-formulation tests a sample of the prepared PAP-containing cores (0.2 g) were added to a standard formulation, either AATCC 1903 standard detergent powder (obtained from James Heal Ltd) or Asda colour formulation (9.8 g). The samples were mixed thoroughly with a spatula and stored in an incubator at 32° C. and 60% relative humidity for a period of 7, 28 and 42 days and then removed to evaluation the remaining PAP content via the titration method described below.

In all cases the evaluations were conducted in triplicate whereby multiple samples were stored in the incubators in order for the complete sample to be evaluated following the allotted time interval. The results for selected particles according to the invention are set forth in Tables 1-7.

As can be seen from Table 6, the comparative example CE1 and the two commercial PAP samples Eureco WM1 and Eureco MG show a marked reduction in stability when compared to the spheroidal particles, such as SP13, which show extremely good stability in powder formulations, in this case Asda colour. Particles SP11, SP12 and SP13 show particularly high stability and their preparation is quick and reproducible when compared to other examples.

Determination of PAP by Iodometric Titration

A sample of the PAP material, either on its own (0.2 g) or in a powder formulation (sufficient core material to give an equivalent of 0.2 g of 100% active PAP in addition to test powder formulation to give a 10 g sample, for example 0.4 g of a core material with 50% activity in combination with 9.6 g of powder formulation), was dissolved in glacial acetic acid (15 mL) and methanol (50 mL), following this potassium iodide (1 g) was added and solution was stirred at room temperature for 20 minutes. The evolved molecular iodine was titrated with a standard 0.1 N sodium thiosulfate solution until the solution remained colourless and the volume of titrant recorded.

The percentage of PAP in each sample was determined from the following calculations.

$$\% \ PAP = \frac{C \times F \times 0.1 \times M \times 100}{W \times 1000 \times 2}$$

C=consumption of sodium thiosulfate
F=correction of titrant (0.1 mol/l $Na_2S_2O_3$)
M=molecular weight of PAP=277.3
W=weight of the sample $$\% \ PAP = \frac{C \times F \times 1.386}{W}$$

C=consumption of sodium thiosulfate
F=correction factor of titrant
W=weight of sample [g]

In each case the level of remaining PAP in the sample was compared to the initial assay after particle formation in order to determine the % activity level. The results for selected particles according to the invention are set forth in Tables 1-7.

Water Content Analysis:

Water content was determined using a Metrohm 701 KF titrino volumetric Karl Fisher titrator.

Screening of the Dissolution of the Materials

In order to assess the viability of the PAP-containing cores, representative samples were screened for their dissolution properties. The following procedure was employed to screen the materials:

A solution of 5 g of liquid detergent in 1 litre of deionised water was prepared. This solution was added to the test cells in a Distek dissolution tester and the solutions were heated to 30° C. and stirred at 250 rpm. The samples to be tested (0.25 g) were then added to the tester and the time noted for complete dissolution was recorded. The results from this screening are represented in Table 8.
Bleach Performance Testing.

In order to assess the performance of the prepared spheroids SP11 was used in a series of wash performance tests in a wash solution, containing 4 g/L Persil Colour powder and compared against a control containing no bleach.
Procedure and Equipment
Persil Colour powder
Stain Cloths: Red Wine—EMPA 114
    Orange Juice—CFT C-S-55
    Tomato Sauce—WFK 1 OSG
    Coffee—CFT C-BC-02
    Tea—EMPA 167
    Grass—EMPA 164
Tergotometer—United States Testing Co. INC
Spectrophotomer—Data Colour International
Method
Wash Liquor:
    Demineralised water was adjusted to 10° French Hard using $CaCl_2$
    The solution pH adjusted to 8.5 using citric acid
    Persil colour powder was added at 4 g/L
    SP 11 was dissolved in the solution at 0.35 g/L Wash Test:
    Stain cloths were cut into 4 g squares (Aprox 14.5 cm×14.5 cm)
    2 colour measurements were obtained per cloth using Spectrophotomer (1 per side) L* a* b* and reflectance at 460 nm
    Each cloth was then washed in a tergotometer (1 L wash liquor per tergo pot) for 30 mins, this was performed at 3 different temperatures 15° C., 20° C. and 40° C.
    Each stain was washed in triplicate and took the average L* a* b* and reflectance at 460 nm reading recorded, again twice per cloth.

Table 9 shows the bleach performance of composition SP11 versus control at various temperatures. As can be seen, SP11 shows effective bleaching performance in this test formulation on a variety of stains, particularly at low temperatures such as in the case for tea stains.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

TABLE 1

Starch containing particles

| | | Components (all expressed as % w/w as dry weigh components) | | | | | Remaining PAP/ | | |
|---|---|---|---|---|---|---|---|---|---|
| Ex. | Starch WM 1 | Polymer (type) | Hostapur SAS 93 (con$^n$ added) | Citric acid | HEDP | Assay (% PAP by weight) | % from original assay (after storage at 40° C.) | | Moisture content/ % w/w |
| | | | | | | | 7 Days | 35 Days | |
| SP1 | 81.83 | (Lycotab C) 3.45 | (Produkt Z1069) 3.45 | (33.33) 7.87 | 2.74 | 0.66 | 63.17 | 98.83 | 98.23 | 0.88 |
| SP2 | 81.73 | (Lycotab PGS) 3.45 | (Produkt Z1069) 3.45 | (33.33) 7.86 | 2.74 | 0.73 | 62.40 | 100.4 | 95.13 | 2.31 |
| SP3 | 82.30 | (Lycotab DSH) 6.33 | (Produkt Z1069) 3.46 | (33.33) 7.38 | 2.74 | 0.66 | 62.30 | 98.39 | 97.11 | 1.10 |
| SP4 | 86.31 | (Potato) 7.28 | — | (33.33) 2.83 | 2.88 | 0.69 | 56.92 | 98.42 | 93.30 | 0.78 |
| SP6 | 81.52 | (Potato) 6.87 | — | (33.33) 8.25 | 2.71 | 0.65 | 56.10 | 96.00 | 82.31 | 1.31 |
| SP6 | 81.18 | (Potato) 6.85 | — | (33.33) 8.59 | 2.70 | 0.68 | 60.70 | 91.10 | 44.15 | 2.19 |
| SP7 | 81.18 | (Potato) 6.85 | — | (33.33) 8.61 | 2.70 | 0.66 | 60.54 | 97.29 | 94.88 | 1.15 |
| SP8 | 85.94 | (Potato) 3.62 | (Luvicross) 3.62 | (33.33) 3.27 | 2.86 | 0.69 | 58.20 | 92.78 | 91.73 | 1.47 |
| SP9 | 81.10 | (Potato) 3.42 | (Luvicross) 3.62 | (33.33) 8.70 | 2.70 | 0.66 | 60.9 | 97.53 | 87.78 | 1.95 |
| SP10 | 81.22 | (Potato) 5.14 | (Produkt Z1069) 1.72 | (33.33) 8.41 | 2.72 | 0.79 | 62.9 | 99.04 | 98.48 | 1.58 |
| SP11 | 81.10 | (Potato) 3.425 | (Produkt Z1069) 3.42 | (33.33) 8.71 | 2.70 | 0.65 | 61.90 | 98.87 | 95.52 | 1.31 |
| SP12 | 80.88 | (Potato) 3.41 | (Produkt Z1069) 3.40 | (33.33) 8.94 | 2.70 | 0.68 | 61.6 | 97.68 | 96.98 | 1.71 |
| SP13 | 80.44 | (Potato) 3.39 | (Produkt Z1069) 3.39 | (33.33) 9.45 | 2.369 | 0.64 | 60.25 | 100.21 | 95.77 | 2.15 |

TABLE 1-continued

Starch containing particles

| Ex. | WM 1 | Starch (type) | Polymer (type) | Hostapur SAS 93 (conⁿ added) | Citric acid | HEDP | Assay (% PAP by weight) | Remaining PAP/ % from original assay (after storage at 40° C.) 7 Days | 35 Days | Moisture content/ % w/w |
|---|---|---|---|---|---|---|---|---|---|---|
| SP14 | 80.38 | (Potato) 3.38 | (Produkt Z1069) 3.40 | (33.33) 9.54 | 2.68 | 0.65 | 61.4 | 98.05 | 96.09 | n/d |
| SP15 | 80.45 | (Roquette Potato Starch) 3.40 | (Produkt Z1069) 3.41 | (33.33) 9.41 | 2.68 | 0.64 | 62.1 | 96.20 | n/d | n/d |
| SP16 | 79.65 | (Maize) 3.35 | (Produkt Z1069) 3.35 | (33.33) 10.35 | 2.65 | 0.64 | 55.55 | 94.98 | 92.25 | 3.40 |
| SP17 | 80.87 | (Maize) 3.41 | (Luvicross) 3.41 | (33.33) 8.94 | 2.70 | 0.68 | 53.34 | 99.12 | 65.90 | 1.90 |
| SP18 | 80.44 | (Rice) 3.39 | (Produkt Z1069) 3.39 | (33.33) 9.40 | 2.71 | 0.67 | 54.50 | 97.76 | 95.30 | 2.37 |
| SP19 | 80.50 | (Rice) 3.39 | (Luvicross) 3.39 | (33.33) 9.34 | 2.71 | 0.67 | 55.10 | 99.07 | 85.84 | 1.52 |
| SP20 | 80.00 | (Wheat) 3.37 | (Produkt Z1069) 3.37 | (33.33) 9.92 | 2.66 | 0.67 | 54.1 | 98.41 | 92.66 | 3.66 |
| SP21 | 80.89 | (Wheat) 3.41 | (Luvicross) 3.41 | (33.33) 8.92 | 2.77 | 0.65 | 56.23 | 97.30 | 75.53 | 1.61 |

TABLE 2

Particles based on different inorganic and polymeric fillers

| Ex | WM 1 | Polymer (1) (type) | Polymer/ Filler (2) (type) | Hostapur SAS 93 (conⁿ added) | Citric acid | HEDP | Assay (% PAP by weight) | Remaining PAP/% from original assay (after storage at 40° C.) 7 Days | 35 Days | Moisture content by Karl-Fisher |
|---|---|---|---|---|---|---|---|---|---|---|
| Eureco WM1 | 100 | — | — | — | — | — | 73.61 | n/d | 96.18 | n/d |
| Eureco MG | n/a | — | — | — | — | — | 66.4 | 100.0 | 91.41 | n/dd |
| CE1* | 85 | (Isomalt) 10 | (Emcosoy) 5.0 | — | — | — | 66.82 | 98.2 | 96.30 | 1.87 |
| SP22 | 88.84 | (Pectin) 7.49 | — | — | 2.97 | 0.7 | 61.20 | 99.51 | 98.20 | 0.70 |
| SP23 | 88.21 | (Pectin) 7.45 | — | (33.33) 0.69 | 2.94 | 0.71 | 61.00 | 98.36 | 96.39 | 1.60 |
| SP24 | 85.73 | (Pectin) 7.24 | — | (33.33) 3.49 | 2.86 | 0.69 | 52.40 | 114.50 | — | 3.80 |
| SP25 | 76.71 | (MCC) 19.15 | — | — | 3.19 | 0.95 | 54.10 | 97.60 | 90.94 | 1.50 |
| SP26 | 85.89 | (MCC) 7.26 | — | (33.33) 2.98 | 2.87 | 1.01 | 57.90 | 95.68 | 84.11 | 1.50 |
| SP27 | 81.35 | (Talc) 3.43 | (Produkt Z1069) 3.43 | (33.33) 8.42 | 2.71 | 0.67 | 54.40 | 97.11 | n/d | 3.49 |
| SP28 | 86.52 | (Ca Bentonite) 7.37 | — | (33.33) 2.50 | 2.91 | 0.70 | 57.30 | 95.29 | 71.06 | 1.13 |
| SP29 | 86.45 | (CO3 Bentonite) 7.29 | — | (33.33) 2.69 | 2.88 | 0.69 | 56.20 | 98.75 | 93.33 | 1.33 |

TABLE 2-continued

Particles based on different inorganic and polymeric fillers

| Ex | WM 1 | Polymer (1) (type) | Polymer/ Filler (2) (type) | Hostapur SAS 93 (con" added) | Citric acid | HEDP | Assay (% PAP by weight) | Remaining PAP/% from original assay (after storage at 40° C.) 7 Days | 35 Days | Moisture content by Karl-Fisher |
|---|---|---|---|---|---|---|---|---|---|---|
| SP30 | 86.43 | (Citrate Bentonite) 7.29 | — | (33.33) 2.70 | 2.89 | 0.69 | 56.30 | 94.49 | 78.86 | 1.09 |
| SP31 | 90.42 | (Citrate Bentonite) 5.83 | — | — | 3.02 | 0.72 | 62.70 | 96.81 | 86.76 | 1.49 |
| SP32 | 82.07 | (Carbopol Ultralez 21) 3.46 | (Isomalt) 6.33 | (33.33) 7.62 | 2.73 | 0.66 | 55.7 | 99.64 | 80.25 | n/d |
| SP33 | 81.11 | (Noveon AA-1) 3.42 | (Potato Starch) 3.42 | (33.33) 8.70 | 2.71 | 0.65 | 59.80 | n/d | 68.28 | 2.17 |
| SP34 | 81.14 | (Noveon AA-1) 3.41 | (Luvicross) 3.41 | (33.33) 8.69 | 2.70 | 0.65 | 60.50 | n/d | 92.15 | 2.17 |
| SP35 | 82.07 | (Ultralez 21) 3.46 | (Isomalt) 3.46 | (33.33) 7.62 | 2.73 | 0.66 | 55.70 | 99.64 | 80.25 | n/d |
| SP36 | 66.87 | (Luvicross) 12.72 | (Isomalt) 12.72 | (20) 4.40 | 2.67 | 0.64 | 54.40 | 97.98 | 94.67 | 2.10 |
| SP37 | 77.53 | (Luvicross) 7.14 | (Isomalt) 7.14 | (20) 4.68 | 2.83 | 0.68 | 46.20 | 95.67 | 79.44 | 3.75 |
| SP38 | 86.44 | (Luvicross) 3.66 | (Isomalt) 3.65 | (33.33) 2.66 | 2.88 | 0.71 | 57.70 | 94.97 | 84.12 | 0.20 |
| SP39 | 82.11 | (Luvicross) 3.46 | (Produkt Z1069) 3.46 | (33.33) 7.57 | 2.74 | 0.66 | 57.07 | 98.70 | 97.60 | 1.70 |
| SP40 | 83.59 | (Kolloidon) 6.20 | (Isomalt) 6.57 | — | 2.94 | 0.71 | 59.20 | 94.59 | 97.30 | 0.90 |
| SP41 | 86.44 | (Kolloidon) 3.64 | (Isomalt) 3.64 | (Polyitaconic acid) 2.68 | 2.91 | 0.69 | 55.65 | 99.55 | 92.15 | 1.84 |
| SP42 | 86.17 | (Kolloidon) 3.65 | (Isomalt) 3.66 | (33.33) 2.85 | 2.88 | 0.78 | 55.50 | 97.30 | 82.85 | 2.49 |
| SP43 | 86.30 | (Kolloidon) 3.65 | (Isomalt) 3.65 | (33.33) 2.74 | 2.88 | 0.78 | 56.30 | 97.34 | 84.97 | 1.85 |
| SP44 | 85.90 | (Kolloidon) 3.62 | (Isomalt) 3.65 | (33.33, Acidified) 3.28 | 2.87 | 0.69 | 54.70 | 97.99 | 89.51 | 2.34 |
| SP45 | 81.94 | (Kolloidon) 3.48 | (Isomalt) 3.46 | (33.33) 7.74 | 2.73 | 0.66 | 55.21 | 101.30 | 95.80 | 1.60 |
| SP46 | 80.75 | (Kolloidon) 2.71 | (Isomalt) 5.48 | (33.33) 7.73 | 2.69 | 0.64 | 56.60 | 98.94 | 94.88 | 1.30 |
| SP47 | 66.84 | (Produkt Z1069) 12.72 | (Isomalt) 12.72 | (20) 4.42 | 2.65 | 0.64 | 44.78 | 90.71 | 75.17 | 7.25 |
| SP48 | 88.83 | (Produkt Z1069) 3.75 | (Isomalt) 3.75 | — | 2.96 | 0.71 | 62.27 | 99.66 | 97.12 | 1.78 |
| SP49 | 82.06 | (Produkt Z1069) 3.46 | (Isomalt) 3.47 | (33.33) 8.80 | 1.49 | 0.71 | 55.6 | 117.03 | 96.04 | 2.56 |
| SP50 | 82.13 | (Produkt Z1069) 3.45 | (Isomalt) 3.46 | (33.33) 7.60 | 2.72 | 0.65 | 58.60 | 100.51 | 97.92 | 1.95 |
| SP51 | 81.02 | (Produkt Z1069) 3.43 | (Isomalt) 3.43 | (33.33) 8.76 | 2.70 | 0.65 | 60.35 | 102.50 | 100 | 1.43 |
| SP52 | 81.32 | (Produkt Z1069) 3.43 | (Isomalt) 3.43 | (33.33) 8.46 | 2.71 | 0.65 | 61.74 | 98.41 | 93.57 | 1.84 |
| SP53 | 80.91 | (Produkt Z1069) 3.41 | (Isomalt) 3.42 | (33.33) 8.91 | 270 | 0.65 | 55.75 | 100.52 | 99.62 | n/d |

TABLE 2-continued

Particles based on different inorganic and polymeric fillers

| Ex | WM 1 | Polymer (1) (type) | Polymer/ Filler (2) (type) | Hostapur SAS 93 (con$^n$ added) | Citric acid | HEDP | Assay (% PAP by weight) | Remaining PAP/% from original assay (after storage at 40° C.) 7 Days | 35 Days | Moisture content by Karl-Fisher |
|---|---|---|---|---|---|---|---|---|---|---|
| SP54 | 80.41 | (XPAA-T5066F) 3.38 | (Potato Starch) 3.38 | (33.33) 9.50 | 2.67 | 0.64 | 59.30 | 100 | 96.12 | 2.18 |

TABLE 3

Particles based on different surfactants or fillers

| Ex | WM 1 | Polymer (1) (type) | Polymer/ Filler (2) (type) | Surfactant [type] (con$^n$ added) | Citric acid | HEDP | Assay (% PAP by weight) | Remaining PAP/% from original assay (after storage at 40° C.) 7 Days | 35 Days | Moisture content by Karl-Fisher |
|---|---|---|---|---|---|---|---|---|---|---|
| SP55 | 86.49 | (Kolloidon) 3.65 | (Isomalt) 3.65 | [2-dodecenyl-succinic anhydride] (33.33) 2.64 | 2.88 | 0.69 | 51.70 | 92.65 | 71.37 | 1.51 |
| SP56 | 85.97 | (Luvicross) 3.62 | (Manitol) 3.62 | [HotapurS93] (33.33) 3.24 | 2.90 | 0.69 | 56.07 | 99.22 | 83.36 | 1.09 |
| SP57 | 87.07 | (Luvicross) 3.67 | (Manitol) 3.67 | [HotapurS93] (33.33) 2.00 | 2.90 | 0.70 | 58.41 | 99.67 | 89.23 | 1.04 |
| SP58 | 86.34 | (Potato Starch) 7.28 | — | [Sorbitol] (33.33) 2.82 | 2.87 | 0.69 | 56.72 | 97.83 | 100.40 | 1.07 |
| SP59 | 81.35 | (Kolloidon) 3.42 | (Isomalt) | [Unithox 450] (33.33) 8.48 | 2.70 | 0.65 | 55.60 | 97.10 | 83.40 | 1.94 |
| SP60 | 80.65 | (Kolloidon) 3.39 | (Isomalt) 3.39 | [Unithox 450] (33.33) 9.26 | 2.68 | 0.64 | 57.13 | 99.98 | 88.97 | 1.68 |
| SP61 | 79.79 | (Kolloidon) 3.38 | (Isomalt) 3.38 | [Unithox 450] (33.33) 10.16 | 2.65 | 0.64 | 57.47 | 98.52 | 78.15 | 1.32 |

TABLE 4

Particles based on different components, or ranges of components

| Ex | WM 1 | Polymer (1) (type) | Polymer/ Filler (2) (type) | Surfactant [type] (con$^n$ added) | Acid (type) | Chelating agent (type) | Assay (% PAP by weight) | Remaining PAP/% from original assay (after storage at 40° C.) 7 Days | 35 Days | Moisture content by Karl-Fisher |
|---|---|---|---|---|---|---|---|---|---|---|
| SP62 | 83.03 | (Roquette Potato Starch) 3.50 | (Produkt Z1069) 3.50 | (Hostapur) 8.30 | (Citric) 1.0 | (HEDP) 0.67 | 56.24 | 100.00 | 88.00 | 2.26 |

TABLE 4-continued

Particles based on different components, or ranges of components

| | | Components (all expressed as % w/w as dry weigh components) | | | | Assay (% PAP by weight) | Remaining PAP/% from original assay (after storage at 40° C.) | | Moisture content by Karl-Fisher |
|---|---|---|---|---|---|---|---|---|---|
| Ex | WM 1 | Polymer (1) (type) | Polymer/ Filler (2) (type) | Surfactant [type] (con" added) | Acid (type) | Chelating agent (type) | 7 Days | 35 Days | |
| SP63 | 79.64 | (Roquette Potato Starch) 3.36 | (Produkt Z1069) 3.36 | (Hostapur) 7.96 | (Citric) 5.04 | (HEDP) 0.64 | 57.51 | 99.67 | 98.55 | 2.64 |
| SP64 | 86.15 | (Roquette Potato Starch) 3.63 | (Produkt Z1069) 3.63 | (Hostapur) 3.01 | (Citric) 2.87 | (HEDP) 0.69 | 60.60 | 100.20 | 98.40 | 2.15 |
| SP65 | 85.25 | (Roquette Potato Starch) 3.60 | (Produkt Z1069) 3.60 | (Hostapur) 4.03 | (Citric) 2.84 | (HEDP) 0.68 | 62.40 | 97.83 | 90.08 | 1.69 |
| SP67 | 82.02 | (Roquette Potato Starch) 3.60 | (Produkt Z1069) 3.60 | (Hostapur) 7.67 | (Ascorbic) 2.73 | (HEDP) 0.66 | 51.40 | 98.30 | 94.90 | 2.22 |
| SP68 | 81.70 | (Roquette Potato Starch) 3.45 | (Produkt Z1069) 3.45 | (Hostapur) 8.03 | — | (HEDP) 3.38* | 59.80 | 94.40 | 95.40 | 2.45 |
| SP69 | 81.59 | (Roquette Potato Starch) 3.44 | (Produkt Z1069) 3.44 | (Hostapur) 8.16 | (phosphoric) 2.72 | (HEDP) 0.65 | 58.23 | 100.40 | 95.80 | 2.88 |
| SP70 | 81.59 | (Roquette Potato Starch) 3.44 | (Produkt Z1069) 3.44 | (Hostapur) 8.16 | (Malic) 2.72 | (HEDP) 0.65 | 59.14 | 95.70 | 84.90 | 2.14 |
| SP71 | 81.53 | (Roquette Potato Starch) 3.44 | (Produkt Z1069) 3.44 | (Hostapur) 7.75 | (Lactic) 2.72 | (HEDP) 0.65 | 57.32 | 100.80 | 96.20 | 1.84 |
| SP72 | 81.41 | (Roquette Potato Starch) 3.44 | (Produkt Z1069) 3.44 | (Hostapur) 8.35 | (δ-Gluconolactone) 2.70 | (HEDP) 0.65 | 58.43 | 96.50 | 93.10 | 2.57 |
| SP73 | 81.41 | (Roquette Potato Starch) 3.43 | (Produkt Z1069) 3.43 | (Hostapur) 8.36 | (Malonic) 2.71 | (HEDP) 0.65 | 59.22 | 97.40 | 96.60 | 1.96 |
| SP74 | 82.03 | (Roquette Potato Starch) 3.46 | (Produkt Z1069) 3.46 | (Hostapur) 7.66 | (Citric) 2.73 | (EDTA) 0.66 | 58.70 | 97.50 | 93.03 | 1.81 |
| SP75 | 82.03 | (Roquette Potato Starch) 3.46 | (Produkt Z1069) 3.46 | (Hostapur) 7.66 | (Citric) 2.73 | (Diss**) 0.66 | 58.02 | 96.36 | 86.98 | N/D |
| SP76 | 82.03 | (Roquette Potato Starch) 3.46 | (Produkt Z1069) 3.46 | (Hostapur) 7.66 | (Citric) 2.73 | (Deq #) 0.66 | 56.02 | 96.20 | 88.10 | N/D |
| SP77 | 82.03 | (Roquette Potato Starch) 3.46 | (Produkt Z1069) 3.46 | (Hostapur) 7.66 | (Citric) 2.73 | (Oxalic acid) 0.66 | 59.03 | 98.98 | 94.81 | N/D |
| SP78 | 81.88 | (Roquette Potato Starch) 3.46 | (poly Itaconic acid) 3.45 | (Hostapur) 7.64 | (Citric) 2.73 | (HEDP) 0.65 | 62.24 | 99.14 | 96.35 | N/D |
| SP79 | 82.03 | (Roquette Potato Starch) 3.46 | (Alginic acid) 3.46 | (Hostapur) 7.65 | (Citric) 2.73 | (HEDP) 0.65 | 57.80 | 98.93 | 95.99 | N/D |

TABLE 5

"Chopped Noodle" formats

| Ex | Produkt WM 1 | Z1069 | Isomalt | Hostapur SAS93 | Citric acid | HEDP | Assay (% PAP by weight) | Remaining PAP/% from original assay (after storage at 40° C.) 7 Days | 35 Days | Moisture content by Karl-Fisher/% w/w |
|---|---|---|---|---|---|---|---|---|---|---|
| CN1 | 81.49 | 3.43 | 3.44 | 8.27 | 2.72 | 0.65 | 55.30 | 99.64 | 93.12 | 2.47 |
| CN2 | 81.38 | 3.42 | 3.43 | 8.34 | 2.71 | 0.69 | 55.00 | 102.40 | 94.23 | 2.12 |

TABLE 6

In-formulation stability results for various particles in Asda Colour Formulation or AATCC standard formulation

| Example | PAP conc. (% w/w) Assay | Asda Colour Formulation 7 days | 28 days | 42 days | AATCC Formulation 7 days | 28 days | 42 days |
|---|---|---|---|---|---|---|---|
| Eureco WM1 | 73.61 | n/d | n/d | n/d | 13.78 | 14.62 | 8.69 |
| Euyreco MG | 66.40 | 65.12 | 37.50 | 15.70 | 89.86 | 73.57 | 62.48 |
| CE1 | 66.82 | 60.78 | 49.45 | 34.67 | n/d | n/d | n/d |
| SP5 | 56.10 | 71.70 | 67.21 | 56.62 | 80.50 | 77.46 | 72.41 |
| SP6 | 60.70 | n/d | n/d | n/d | 88.63 | 62.43 | 63.14 |
| SP9 | 60.90 | n/d | n/d | n/d | 83.69 | 69.73 | 63.37 |
| SP10 | 62.60 | n/d | n/d | n/d | 90.96 | 90.17 | 73.39 |
| SP11 | 61.90 | n/d | n/d | n/d | 89.52 | 88.98 | 84.32 |
| SP12 | 61.58 | n/d | n/d | n/d | 94.46 | 89.50 | 81.69 |
| SP13 | 60.47 | 92.01 | 83.02 | 75.15 | n/d | n/d | n/d |
| SP16 | 54.09 | n/d | n/d | n/d | 82.71 | 71.85 | 54.49 |
| SP19 | 54.54 | n/d | n/d | n/d | 82.72 | 66.72 | 68.78 |
| SP49 | 55.60 | 65.07 | 55.11 | 43.93 | n/d | n/d | n/d |
| SP50 | 56.12 | 63.42 | 57.22 | 40.62 | n/d | n/d | n/d |
| SP51 | 61.48 | 88.35 | 80.64 | 70.53 | 93.12 | 86.06 | 73.12 |
| SP52 | 60.19 | n/d | n/d | n/d | 97.35 | 88.71 | 86.20 |
| SP53 | 55.75 | 72.53 | 54.10 | 42.15 | 89.91 | 87.17 | 81.80 |
| SP68 | 59.80 | n/d | n/d | n/d | 95.50 | 92.00 | 87.10 |
| SP69 | 58.23 | n/d | n/d | n/d | 93.70 | 88.70 | 71.20 |
| SP72 | 58.43 | n/d | n/d | n/d | 96.20 | 85.90 | 70.20 |
| CN1 | 55.30 | 68.35 | 63.91 | 66.66 | n/d | n/d | n/d |
| CN2 | 55.00 | 66.16 | 65.89 | 61.00 | n/d | n/d | n/d |

TABLE 7

Stability of coated spheroids and chopped noodles in powder formulations

| Core material to be coated | PAP core stability after 5 weeks at 40° C./% | Coated Material | Polymer coating applied (amount % w/w) | PAP content after coating/% of PAP w/w | Asda Colour Formulation 7 days | 28 days | 42 days | AATCC Formulation 7 days | 28 days | 42 days |
|---|---|---|---|---|---|---|---|---|---|---|
| SP53a | 98.22 | CP1 | Vy260/AGC emulsion with top-coat of PVB (10-98) [25% w/w coating of emulsion with 2.5% w/w of topcoat] | 34.96 | 76.2 | 68.49 | 57.45 | n/d | n/d | n/d |
| | | CP2 | Mowiol®-PVOH (3-85) [4.0] | 50.82 | 68.9 | 76.07 | 66.19 | n/d | n/d | n/d |
| SP53b | 95.92 | CP3 | Mowiol®-PVOH (4-98) [4.2] | 51.67 | 68.71 | 75.34 | 58.20 | n/d | n/d | n/d |
| | | CP4 | Mowiol®-PVOH (10-98) [2.8] | 55.85 | 73.46 | 59.04 | 73.75 | n/d | n/d | n/d |
| | | CP5 | Mowiol® PVOH(30-98) [1.6] | 54.48 | 82.80 | 73.88 | 64.74 | n/d | n/d | n/d |
| SP53c | 96.61 | CP6 | 8% Butyrated Mowiol® PVOH (4-98) [3.2] | 51.52 | 84.52 | 93.4 | 52.33 | n/d | n/d | n/d |
| | | CP7 | 8% Butyrated Mowiol® PVOH (10-98) [3.4] | 52.78 | 72.28 | 72.27 | 69.75 | n/d | n/d | n/d |

TABLE 7-continued

Stability of coated spheroids and chopped noodles in powder formulations

| Core material to be coated | PAP core stability after 5 weeks at 40° C./% | Coated Material | Polymer coating applied (amount % w/w) | PAP content after coating/ % of PAP w/w | Stability based on initial Assay % (w/w) 32° C., 60% RH | | | | | |
|---|---|---|---|---|---|---|---|---|---|---|
| | | | | | Asda Colour Formulation | | | AATCC Formulation | | |
| | | | | | 7 days | 28 days | 42 days | 7 days | 28 days | 42 days |
| | | CP8 | 8% Butyrated Mowiol ® PVOH (30-98) [3.0] | 54.95 | 69.54 | 69.02 | 55.96 | n/d | n/d | n/d |
| | | CP9 | 5% Butyrated Mowiol ® PVOH (4-98) [2.8] | 51.48 | 78.86 | 75.42 | 66.60 | n/d | n/d | n/d |
| | | CP10 | 20% Butyrated Mowiol ® PVOH (4-98) neutralised [1.4] | 51.49 | 67.11 | 65.60 | 44.08 | n/d | n/d | n/d |
| | | CP11 | 20% Butyrated Mowiol ® PVOH(4-98) un neutralised [4.2] | 51.47 | 69.83 | 66.44 | 55.73 | n/d | n/d | n/d |
| SP53d | 96.61 | CP12 | 5% Butyrated Mowiol ® PVOH (4-98) un neutralised [3.4] | 52.28 | 89.24 | 88.73 | 85.40 | n/d | n/d | n/d |
| SP53e | 96.20 | CP13 | 20% Butyrated Mowiol ® PVOH (4-98) un neutralised [1.9] | 51.89 | n/d | n/d | n/d | 88.90 | 72.91 | 83.33 |
| | | | 5% Butyrated Mowiol ® PVOH (4-88) un neutralised [3.4] | 51.64 | n/d | n/d | n/d | 87.15 | 86.73 | 89.06 |
| SP53f | 96.20 | CP14 | 5% Butyrated Mowiol ® PVOH (4-88) neutralised [3.3] | 52.12 | n/d | n/d | n/d | 86.89 | 87.76 | 87.46 |
| | | CP15 | Mowiol ® PVOH (4-98) [3.8] | 51.13 | n/d | n/d | n/d | 91.92 | 89.00 | 85.47 |
| | | CP16 | 10% Butyrated Mowiol ® PVOH (4-88) neutralised [4.8] | 50.89 | n/d | n/d | n/d | 93.31 | 86.82 | 85.23 |
| | | CP17 | 10% Butyrated Mowiol ® PVOH (4-88) neutralised [2.0] | 51.11 | n/d | n/d | n/d | 93.20 | 89.76 | 83.19 |
| SP53g | 96.20 | CP18 | 10% Butyrated Mowiol ® PVOH (4-88) neutralised [3.6] | 59.15 | n/d | n/d | n/d | 93.54 | 87.17 | 84.25 |
| | | CP19 | 8% Butyrated Mowiol ® PVOH (3-85) neutralised [3.6] | 59.15 | n/d | n/d | n/d | 92.27 | 85.68 | 83.19 |
| | | CP20 | 8% Butyrated Mowiol ® PVOH (3-85) un-neutralised [1.6] | 60.55 | n/d | n/d | n/d | 92.27 | 87.90 | 83.05 |
| | | CP21 | 8% Butyrated Mowiol ® PVOH (3-85) neutralised [3.6] | 525.27 | n/d | n/d | n/d | 83.97 | 73.14 | 55.25 |
| | | CP22 | 5% Butyrated Mowiol ® PVOH (15-99) neutralised [4.2] | 59.34 | n/d | n/d | n/d | 86.82 | 87.94 | 85.56 |
| | | CP23 | 5% Butyrated Mowiol ® PVOH (15-99) neutralised [2.4] | 58.90 | n/d | n/d | n/d | 89.45 | 73.14 | 83.21 |
| SP7a | 94.60 | CP24 | 20% Butyrated Mowiol ® PVOH (3-85) neutralised [4.4] | 56.414 | n/d | n/d | n/d | 87.84 | 73.69 | n/d |
| | | CP25 | 30% Butyrated Mowiol ® PVOH (3-85) neutralised [2.2] | 56.71 | n/d | n/d | n/d | 84.59 | 72.86 | n/d |
| | | CP26 | 5% Butyrated Mowiol ® PVOH (18-88) neutralised [4.4] | 57.10 | n/d | n/d | n/d | 85.57 | n/d | n/d |
| | | CP27 | 20% Butyrated Mowiol ® PVOH (1-98) neutralised [1.2] | 56.41 | n/d | n/d | n/d | 87.63 | 71.10 | n/d |
| | | CP28 | 20% Butyrated Mowiol ® PVOH (10-98) neutralised [1.2] | 56.41 | n/d | n/d | n/d | 87.63 | 71.10 | n/d |
| | | CP29 | 30% Butyrated Mowiol ® PVOH (10-98) neutralised [4.0] | 57.36 | n/d | n/d | n/d | 86.17 | n/d | n/d |

TABLE 7-continued

Stability of coated spheroids and chopped noodles in powder formulations

| Core material to be coated | PAP core stability after 5 weeks at 40° C./% | Coated Material | Polymer coating applied (amount % w/w) | PAP content after coating/ % of PAP w/w | Stability based on initial Assay % (w/w) 32° C., 60% RH | | | | | |
|---|---|---|---|---|---|---|---|---|---|---|
| | | | | | Asda Colour Formulation | | | AATCC Formulation | | |
| | | | | | 7 days | 28 days | 42 days | 7 days | 28 days | 42 days |
| | | CP30 | 8% Butyrated Mowiol ® PVOH (30-98) neutralised [4.2] | 56.22 | n/d | n/d | n/d | 87.06 | 71.84 | n/d |
| SP11 | 95.50 | CP31 | 5% Butyrated Mowiol ® PVOH (4-98) un-neutralised [12.3] | 57.31 | n/d | n/d | n/d | 93.46 | 86.80 | 84.02 |

TABLE 8

Dissolution properties of the spheroids

| Sample | Time for complete dissolution/seconds |
|---|---|
| Eureco WM1 | 900 |
| Eureco MG | >900 s |
| SP5 | 90 |
| SP17 | 50 |
| SP19 | 150 |
| SP45 | 30 |
| SP46 | 60 |
| SP53c | 360 |
| SP68 | 120 |
| SP69 | 120 |
| SP72 | 120 |
| SP74 | 90 |
| CN1 | 40 |
| CN2 | 40 |

TABLE 9

Bleach performance of SP11 vs control at various temperatures

| Stain/(% reflectance c.f. unwashed test cloth | | Wine | Tea | Grass | Oily Tomato Sauce | Orange Juice | Coffee |
|---|---|---|---|---|---|---|---|
| Control | 15° C. | 43.5 | 27.4 | 38.3 | 39.8 | 72.0 | 50.0 |
| | 20° C. | 42.4 | 29.0 | 39.3 | 39.8 | 73.3 | 50.8 |
| | 40° C. | 55.7 | 29.1 | 45.6 | 41.1 | 74.8 | 50.6 |
| SP11 | 15° C. | 70.0 | 58.5 | 54.8 | 41.8 | 78.8 | 57.6 |
| | 20° C. | 71.5 | 61.6 | 57.9 | 42.6 | 79.2 | 59.2 |
| | 40° C. | 79.8 | 70.6 | 67.5 | 45.7 | 83.5 | 64.0 |

The invention claimed is:

1. An extruded particle obtained by a process comprising the steps of:
   (1) forming a mixture consisting of
      (a) at least one bleaching agent comprising 6-phthalimido-peroxy-hexanoic acid
      (bi) at least one component selected from potato starch, pregellatinised potato starch, maize starch, wheat starch, rice starch and partially pregellatinised maize starch;
         or
         sucrose, mannitol, isomalt, xylitol, sorbitol, trehalose and lactitol;
      (bii) at least one component selected from linear, branched and cross-linked polymers and copolymers selected from a functionalised poly(vinyl) alcohol, a linear, branched or cross-linked polymer or copolymer prepared from one or more of the following monomers: (meth)acrylic acid, acrylic acid, maleic acid, fumaric acid, itaconic acid, 2-acrylamido-2-methyl-1-propane-sulfonic acid, and vinyl acetate;
      (c) at least one pH reducing agent selected from citric acid, tartaric acid, tartronic acid, oxalic acid, maleic acid, itaconic acid, malonic acid, fumaric acid, hydrochloric acid, sulfuric acid, phosphoric acid, gluconic acid, lactic acid, toluene sulfonic acid, ascorbic acid, acetic acid, and methane sulfonic acid; and
      (d) at least one chelating agent selected from ethylenediaminetetraacetic acid (EDTA), glutamic acid diacetic acid (GLDA), diethylene triamine pentaacetic acid (DTPA), hydroxyethylethylenediaminetriacetic acid (HEDTA), nitrilotriacetic acid (NTA), ethanoldiglycinic acid (EDG), 2,2',2'',2''-(1,2-propanediyldinitrilo) tetraacetic acid (PDTA), glucoheptonate, N,N-bis(carboxymethyl)-L-glutamic acid, nitroacetic acid, phosphoric acid and polymers of phosphoric acid, aminopolyphosphonic acid, 1-hydroxyethylene-1, 1-diphosphonic acid (HEDP), diethylenetrianime penta(methylene phosphonic acid) (DTPMP), the sodium salt of diethylene triamine penta (methylene phosphonic acid), 2-phosphonobutane-1,2,4-tricarboxylic acid and amino tri(methylene phosphonic acid (ATMP);
   (2) extruding the mixture obtained in step (1);
   (3) processing the extruded mixture obtained in step (2) to form the extruded particle; and
   (4) drying the particle obtained in step (3).

2. The extruded particle according to claim 1 wherein the pH reducing agent is citric acid.

3. The extruded particle according to claim 1 wherein the chelating agent is 1-hydroxy-ethylene-1,1-diphosphonic acid (HEDP).

4. The extruded particle according to claim 1 wherein the at least one component is pregellatinised potato starch.

5. The extruded particle according to claim 1 wherein the linear, branched or cross-linked polymer or copolymer is selected from polyacrylic acid, poly(meth)acrylic acid and cross-linked polyacrylic acid.

6. The extruded particle according to claim 5 wherein the linear, branched or cross-linked polymer or copolymer is cross-linked polyacrylic acid.

7. The extruded particle according to claim 1 which is substantially free from boron.

8. A composition comprising the extruded particle according to claim 1.

9. A composition according to claim 8 which is a laundry detergent, an auto-dishwasher product or a cleaning composition.

10. A composition according to claim 8 which is a solid.

11. A composition according to claim 8 which is a liquid.

12. The extruded particle according to claim 1 which is spheroidal.

13. The extruded particle according to claim 1, wherein the particle comprises 40 to 80% by weight, relative to the total weight of the particle, of the at least one bleaching agent.

14. The extruded particle according to claim 1, wherein the particle comprises less than 100 ppm of boron.

15. The extruded particle according to claim 1, wherein the at least one component is potato starch.

* * * * *